(12) United States Patent
Dattagupta et al.

(10) Patent No.: US 6,596,489 B2
(45) Date of Patent: Jul. 22, 2003

(54) METHODS AND COMPOSITIONS FOR ANALYZING NUCLEOTIDE SEQUENCE MISMATCHES USING RNASE H

(75) Inventors: Nanibhushan Dattagupta, San Diego, CA (US); Ta-Chien Tseng, Miao-Li Hsin (TW)

(73) Assignee: Applied Gene Technologies, San Diego, CA (US)

( * ) Notice: Subject to any disclaimer, the term of this patent is extended or adjusted under 35 U.S.C. 154(b) by 0 days.

(21) Appl. No.: 09/823,634

(22) Filed: Mar. 30, 2001

(65) Prior Publication Data

US 2002/0142308 A1 Oct. 3, 2002

(51) Int. Cl.$^7$ .......................... C12Q 1/68; C12P 19/34; C12N 9/00; C07H 21/04
(52) U.S. Cl. .......................... 435/6; 435/91.1; 435/91.2; 435/183; 536/23.1; 536/24.3
(58) Field of Search .......................... 435/6, 91.2, 183.7, 435/91.1, 183; 536/23.1, 353, 24.3; 530/300

(56) References Cited

U.S. PATENT DOCUMENTS

| | | |
|---|---|---|
| 4,683,195 A | 7/1987 | Mullis et al. |
| 4,683,202 A | 7/1987 | Mullis |
| 5,143,854 A | 9/1992 | Pirrung et al. |
| 5,288,514 A | 2/1994 | Ellman |
| 5,312,233 A | 5/1994 | Tanny et al. |
| 5,384,261 A | 1/1995 | Winkler et al. |
| 5,409,818 A | 4/1995 | Davey et al. |
| 5,541,061 A | 7/1996 | Fodor et al. |
| 5,541,313 A | 7/1996 | Ruth |
| 5,554,517 A | 9/1996 | Davey et al. |
| 5,556,752 A | 9/1996 | Lockhart et al. |
| 5,561,071 A | 10/1996 | Hollenberg et al. |
| 5,587,472 A | 12/1996 | Dattagupta et al. |
| 5,607,834 A | 3/1997 | Bagwell |
| 5,652,357 A | 7/1997 | Newman et al. |
| 5,660,988 A * | 8/1997 | Duck et al. ............ 435/6 |
| 5,670,337 A | 9/1997 | Newman et al. |
| 5,677,195 A | 10/1997 | Winkler et al. |
| 5,719,026 A | 2/1998 | Fukui et al. |
| 5,741,644 A | 4/1998 | Kambara et al. |
| 5,830,664 A * | 11/1998 | Rosemeyer et al. ....... 435/6 |
| 5,861,242 A | 1/1999 | Chee et al. |
| 5,866,336 A | 2/1999 | Nazarenko et al. |
| 5,972,601 A | 10/1999 | Newman |
| 6,001,653 A | 12/1999 | Crooke et al. |
| 6,024,138 A | 2/2000 | Fritz et al. |
| 6,040,138 A * | 3/2000 | Lockhart et al. .......... 435/6 |
| 6,071,734 A | 6/2000 | Yoon et al. |
| 6,346,385 B1 | 2/2002 | Eguchi et al. |
| 2002/0034747 A1 * | 3/2001 | Bruchez et al. .......... 435/6 |

FOREIGN PATENT DOCUMENTS

| | | |
|---|---|---|
| CA | 2189638 | 11/1995 |
| WO | WIO 95/30772 | 11/1995 |
| WO | WO 98/07869 | 2/1998 |
| WO | WO 99/28447 | 6/1999 |
| WO | WO 99/31271 | 6/1999 |
| WO | WO 00/73322 | 12/2000 |

OTHER PUBLICATIONS

Chee et al. (1996) *Science* 274:610–614.
Beaucage and Carruthers, *Tetrahedron Lett.*, 22:1859–1862 (1981).
Beenhouwer et al., *Tubercule and Lung Disease*, 76:425–430 (1995).
Berkower et al., *J. Biol. Chem.*, 248(17):5914–21 (1973).
Blok and Kramer, *Molecular and Cellular Probes*, 11:187–194 (1997).
Crooke, *Antisense nucleic Acid Drug Dev.*, 8(2):133–4 (1998).
Dattagupta et al., *Analytical Biochemistry*, 177:85–89(1989).
Donis–Keller, *Nucleic Acids Res.*, 7(1):179–92 (1979).
Fujiwara and Oishi, *Nucleic Acids Res.*, 26:5728–5733 (1998).
Gravitt et al., *J. Clin. Micro.*, 36:3020–3027(1998).
Kanehisa, *Nucleic Acids Res.*, 12:203 (1984).
Matteucci et al., *J. Am. Chem. Soc.*, 103:3185 (1981).
Mergny et al., *Nucleic Acids Res.*, 22:920–928 (1994).
Papaphilis et al., *Anticancer Res.*, 10(5A):1201–12 (1990).
Saiki et al., *Proc. Natl. Acad. Sci. USA*, 86:6230–6234(1989).
Sriprakash and Hartas, *Gene Anal. Techn.*, 6:29–32 (1989).
Telenti et al., *Lancet*, 341:647–650 (1993).
Watson et al., *Molecular Biology of the Gene*, 4th Edition, 1987, The Bejacmin/Cummings Pub. co., p. 224.
Yang and Steitz, *Structure*, 3(2):131–4 (1995).

* cited by examiner

*Primary Examiner*—Kenneth R. Horlick
*Assistant Examiner*—Young Kim
(74) *Attorney, Agent, or Firm*—Morrison & Foerster LLP

(57) ABSTRACT

This invention relates generally to nucleic acid hybridization analysis. More specifically, a method for detecting a point mutation in a DNA strand is provided, which method uses, inter alia, a test nucleic acid strand complementary to a target DNA strand, said nucleic acid strand comprises a sufficient number of ribonucleotide residues that span the position of said point mutation to be detected to form a target DNA strand/test nucleic acid strand duplex and RNase H cleavage of said target DNA strand/test nucleic acid strand duplex. Kits and arrays for detecting a point mutation in a DNA strand comprising test nucleic acid strand comprising a sufficient number of ribonucleotide residues that span the position of said point mutation to be detected are also provided.

22 Claims, 7 Drawing Sheets

Figure 3
```
AGT02008:  5'-TTTTTTTAAAATTTTTTTTT-3' (SEQ ID NO:8)
AGT02012:  5'-TTTTTTTAAAATTTTTTTT-3'  (SEQ ID NO:9)
AGT02013:  5'-TTTTTTTAAAATTTTTTTTT-3' (SEQ ID NO:10)
AGT02014:  5'-TTTTTTTAAAATTTTTTTT-3'  (SEQ ID NO:11)
AGT02009:  3'-AAAAAATTTTAAAAAAAA-5'   (SEQ ID NO:12)
```
(3A)
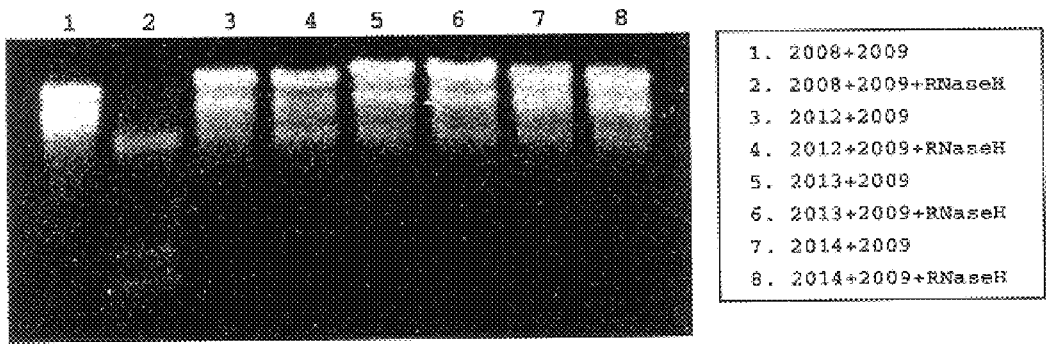
1. 2008+2009
2. 2008+2009+RNaseH
3. 2012+2009
4. 2012+2009+RNaseH
5. 2013+2009
6. 2013+2009+RNaseH
7. 2014+2009
8. 2014+2009+RNaseH
(3B)
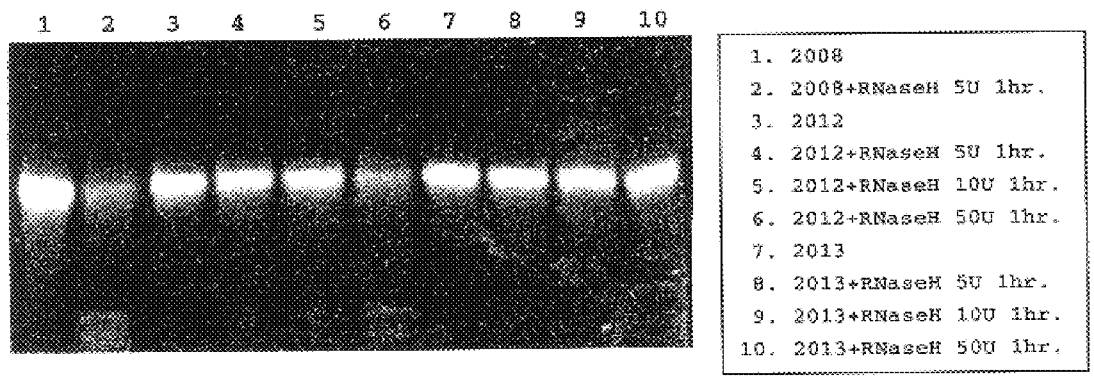
1. 2008
2. 2008+RNaseH 5U 1hr.
3. 2012
4. 2012+RNaseH 5U 1hr.
5. 2012+RNaseH 10U 1hr.
6. 2012+RNaseH 50U 1hr.
7. 2013
8. 2013+RNaseH 5U 1hr.
9. 2013+RNaseH 10U 1hr.
10. 2013+RNaseH 50U 1hr.

Figure 4

```
AGT02008:   5'-TTTTTTTAAAATTTTTTTTT-3' (SEQ ID NO:8)
AGT02009:   3'-AAAAAAATTTTAAAAAAAAA-5' (SEQ ID NO:12)
AGT02020:   3'-AAAAAAAGTTTAAAAAAAAA-5' (SEQ ID NO:13)
AGT02021:   3'-AAAAAAATGTTAAAAAAAAA-5' (SEQ ID NO:14)
AGT02022:   3'-AAAAAAAGGTTAAAAAAAAA-5' (SEQ ID NO:15)
AGT02023:   3'-AAAAAAAGTGTAAAAAAAAA-5' (SEQ ID NO:16)
AGT02024:   3'-AAAAAAATCTTAAAAAAAAA-5' (SEQ ID NO:17)
AGT02025:   3'-AAAAAAATATTAAAAAAAAA-5' (SEQ ID NO:18)
```

(4A)

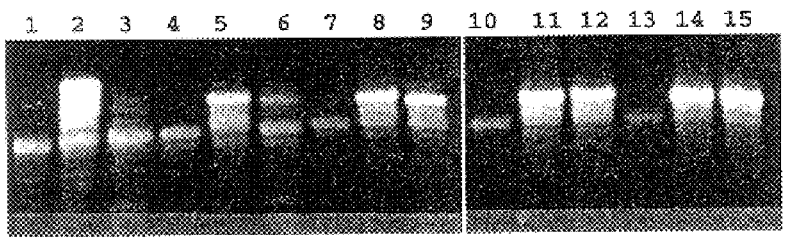

1. 2009
2. 2008+2009
3. 2008+2009+RNaseH
4. 2020
5. 2008+2020
6. 2008+2020+RNaseH
7. 2021
8. 2008+2021
9. 2008+2021+RNaseH
10. 2022
11. 2008+2022
12. 2008+2022+RNaseH
13. 2023
14. 2008+2023
15. 2008+2023+RNaseH (4B)

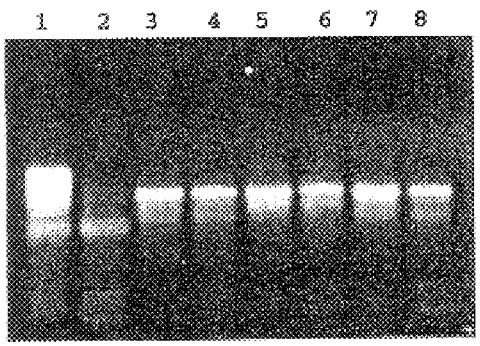

1. 2008+2009
2. 2008+2009+RNaseH
3. 2008+2021
4. 2008+2021+RNaseH
5. 2008+2024
6. 2008+2024+RNaseH
7. 2008+2025
8. 2008+2025+RNaseH

Figure 5

```
AGT02010:(SEQ ID NO:19)  ---loop---
5'-GCACATTCTCAUCUCTGAAAACTTCCGTGGTTTCAGAGATGAGAATGTGC-3'
AGT02028:(SEQ ID NO:21)
3'-CGTGTAAGAGTTAAGACTTTTGAAGGCACC-5'

AGT02011:(SEQ ID NO:20)  ---loop---
5'-GCACATTCTCATCTCTGAAAACTTCCGTGGTTTCAGAGAUGAGAATGTGC-3'
AGT02029:(SEQ ID NO:22)
3'-AAGGCACCAAAGTCTAGACTCTTACACG-5'
```

(5A)

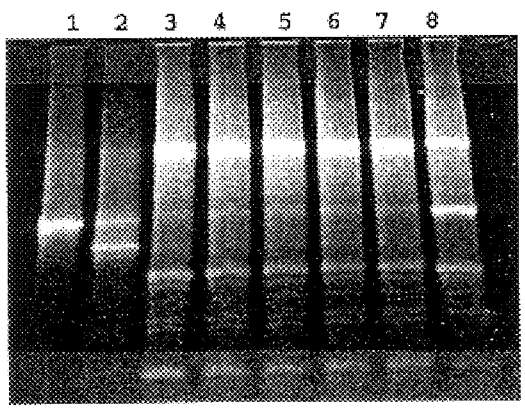

| | anneal temp.(C) |
|---|---|
| 1. 2010 | |
| 2. 2010+RNaseH | |
| 3. 2010+2028+RNaseH | 60.2 |
| 4. 2010+2028+RNaseH | 64.5 |
| 5. 2010+2028+RNaseH | 69.6 |
| 6. 2010+2028+RNaseH | 74.8 |
| 7. 2010+2028+RNaseH | 79.9 |
| 8. 2010+2028 | 79.9 |

(5B)

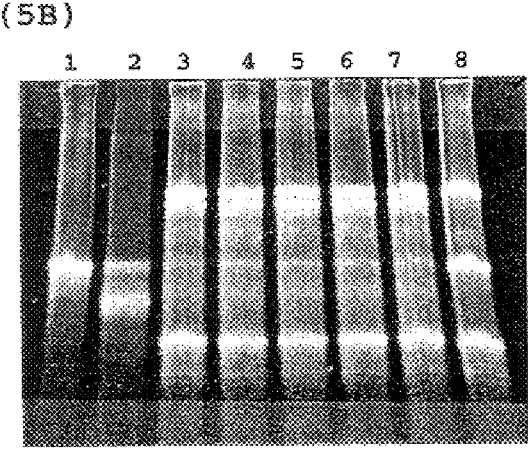

| | anneal temp.(C) |
|---|---|
| 1. 2011 | |
| 2. 2011+RNaseH | |
| 3. 2011+2029+RNaseH | 60.2 |
| 4. 2011+2029+RNaseH | 64.5 |
| 5. 2011+2029+RNaseH | 69.6 |
| 6. 2011+2029+RNaseH | 74.8 |
| 7. 2011+2029+RNaseH | 79.9 |
| 8. 2011+2029 | 79.9 |

Figure 6
```
AGT02010:(SEQ ID NO:19)  --loop--
5'-GCACATTCTCAUCUCTGAAAACTTCCGTGGTTTCAGAGATGAGAATGTGC-3'
AGT02028:(SEQ ID NO:21)
3'-CGTGTAAGAGTTAAGACTTTTGAAGGCACC-5'
```
(6A)
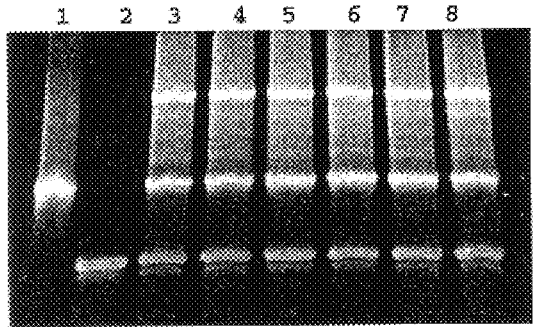
| | | anneal temp.(C) |
|---|---|---|
| 1. | 2010 | |
| 2. | 2028 | |
| 3. | 2010+2028 | 37 |
| 4. | 2010+2028 | 47 |
| 5. | 2010+2028 | 55 |
| 6. | 2010+2028 | 65 |
| 7. | 2010+2028 | 75 |
| 8. | 2010+2028 | 85 |
(6B)
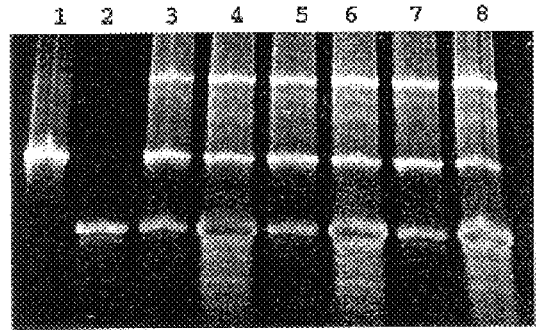
| | | | anneal temp.(C) |
|---|---|---|---|
| 1. | 2010 | | |
| 2. | 2028 | (μg) | |
| 3. | 2010+2028 | (0.25) | 18 |
| 4. | 2010+2028 | (3) | 18 |
| 5. | 2010+2028 | (0.25) | 25 |
| 6. | 2010+2028 | (3) | 25 |
| 7. | 2010+2028 | (0.25) | 30 |
| 8. | 2010+2028 | (3) | 30 |
(6C)
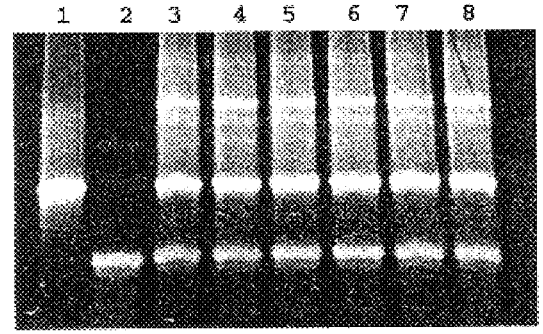
| | | | anneal temp.(C) |
|---|---|---|---|
| 1. | 2010 | | |
| 2. | 2028 | (min) | |
| 3. | 2010+2028 | (1) | room temp |
| 4. | 2010+2028 | (2) | room temp |
| 5. | 2010+2028 | (3) | room temp |
| 6. | 2010+2028 | (4) | room temp |
| 7. | 2010+2028 | (5) | room temp |
| 8. | 2010+2028 | (10) | 4 |

SEQUENCE LISTING

<160> NUMBER OF SEQ ID NOS: 27

<210> SEQ ID NO 1
<211> LENGTH: 21
<212> TYPE: DNA
<213> ORGANISM: Artificial Sequence
<220> FEATURE:
<223> OTHER INFORMATION: Oligonucleotide

<400> SEQUENCE: 1
catccgtaac tacatcttcc a                                          21

<210> SEQ ID NO 2
<211> LENGTH: 51
<212> TYPE: DNA
<213> ORGANISM: Artificial Sequence

```
<220> FEATURE:
<223> OTHER INFORMATION: Oligonucleotide

<400> SEQUENCE: 2
catccgtaac tacatcttcc atttttttttt tggaagatgt agttacggat g        51

<210> SEQ ID NO 3
<211> LENGTH: 25
<212> TYPE: DNA
<213> ORGANISM: Artificial Sequence
<220> FEATURE:
<223> OTHER INFORMATION: Primer

<400> SEQUENCE: 3
gagaattcgg tcggcgagct gatcc                                      25

<210> SEQ ID NO 4
<211> LENGTH: 24
<212> TYPE: DNA
<213> ORGANISM: Artificial Sequence
<220> FEATURE:
<223> OTHER INFORMATION: Primer

<400> SEQUENCE: 4
cgaagcttga cccgcgcgta cacc                                       24

<210> SEQ ID NO 5
<211> LENGTH: 57
<212> TYPE: DNA
<213> ORGANISM: Artificial Sequence
<220> FEATURE:
<223> OTHER INFORMATION: Long hairpin probe

<400> SEQUENCE: 5
caattcatgg accagaacaa cccgtttttt tttcgggttg ttctgctcca tgaattg    57

<210> SEQ ID NO 6
<211> LENGTH: 18
<212> TYPE: DNA
<213> ORGANISM: Artificial Sequence
<220> FEATURE:
<223> OTHER INFORMATION: Immobilized oligonucleotide

<400> SEQUENCE: 6
tttttttttc aattcatg                                              18

<210> SEQ ID NO 7
<211> LENGTH: 48
<212> TYPE: DNA
<213> ORGANISM: Artificial Sequence
<220> FEATURE:
<223> OTHER INFORMATION: Phosphorylated oligonucleotide

<400> SEQUENCE: 7
gaccagaaca acccgttttt ttttcgggtt gttctgctcc atgaattg              48

<210> SEQ ID NO 8
<211> LENGTH: 20
<212> TYPE: DNA
<213> ORGANISM: Artificial Sequence
<220> FEATURE:
<223> OTHER INFORMATION: Oligonucleotide AGT02008

<400> SEQUENCE: 8
tttttttaaa atttttttttt                                           20
```

```
<210> SEQ ID NO 9
<211> LENGTH: 20
<212> TYPE: DNA
<213> ORGANISM: Artificial Sequence
<220> FEATURE:
<223> OTHER INFORMATION: Oligonucleotide AGT02012

<400> SEQUENCE: 9
tttttttaaa attttttttt                                               20

<210> SEQ ID NO 10
<211> LENGTH: 20
<212> TYPE: DNA
<213> ORGANISM: Artificial Sequence
<220> FEATURE:
<223> OTHER INFORMATION: Oligonucleotide AGT02013

<400> SEQUENCE: 10
tttttttaaa attttttttt                                               20

<210> SEQ ID NO 11
<211> LENGTH: 20
<212> TYPE: DNA
<213> ORGANISM: Artificial Sequence
<220> FEATURE:
<223> OTHER INFORMATION: Oligonucleotide AGT02014

<400> SEQUENCE: 11
tttttttaaa attttttttt                                               20

<210> SEQ ID NO 12
<211> LENGTH: 20
<212> TYPE: DNA
<213> ORGANISM: Artificial Sequence
<220> FEATURE:
<223> OTHER INFORMATION: Complement DNA oligo AGT02009

<400> SEQUENCE: 12
aaaaaaaaat tttaaaaaaa                                               20

<210> SEQ ID NO 13
<211> LENGTH: 20
<212> TYPE: DNA
<213> ORGANISM: Artificial Sequence
<220> FEATURE:
<223> OTHER INFORMATION: Oligo AGT02020

<400> SEQUENCE: 13
aaaaaaaaat ttgaaaaaaa                                               20

<210> SEQ ID NO 14
<211> LENGTH: 20
<212> TYPE: DNA
<213> ORGANISM: Artificial Sequence
<220> FEATURE:
<223> OTHER INFORMATION: Oligo AGT02021

<400> SEQUENCE: 14
aaaaaaaaat tgtaaaaaaa                                               20

<210> SEQ ID NO 15
<211> LENGTH: 20
<212> TYPE: DNA
<213> ORGANISM: Artificial Sequence
<220> FEATURE:
<223> OTHER INFORMATION: Oligo AGT02022
```

<400> SEQUENCE: 15
aaaaaaaaat tggaaaaaaa                                              20

<210> SEQ ID NO 16
<211> LENGTH: 20
<212> TYPE: DNA
<213> ORGANISM: Artificial Sequence
<220> FEATURE:
<223> OTHER INFORMATION: Oligo AGT02023

<400> SEQUENCE: 16
aaaaaaaaat gtgaaaaaaa                                              20

<210> SEQ ID NO 17
<211> LENGTH: 20
<212> TYPE: DNA
<213> ORGANISM: Artificial Sequence
<220> FEATURE:
<223> OTHER INFORMATION: Oligo AGT02024

<400> SEQUENCE: 17
aaaaaaaaat tctaaaaaaa                                              20

<210> SEQ ID NO 18
<211> LENGTH: 20
<212> TYPE: DNA
<213> ORGANISM: Artificial Sequence
<220> FEATURE:
<223> OTHER INFORMATION: Oligo AGT02025

<400> SEQUENCE: 18
aaaaaaaaat tataaaaaaa                                              20

<210> SEQ ID NO 19
<211> LENGTH: 50
<212> TYPE: DNA
<213> ORGANISM: Artificial Sequence
<220> FEATURE:
<221> NAME/KEY: DNA/RNA hybrid
<222> LOCATION: (1) ... (50)
<223> OTHER INFORMATION: Oligo AGT02010

<400> SEQUENCE: 19
gcacattctc aucuctgaaa acttccgtgg tttcagagat gagaatgtgc              50

<210> SEQ ID NO 20
<211> LENGTH: 50
<212> TYPE: DNA
<213> ORGANISM: Artificial Sequence
<220> FEATURE:
<221> NAME/KEY: DNA/RNA hybrid
<222> LOCATION: (1) ... (50)
<223> OTHER INFORMATION: Oligo AGT02011

<400> SEQUENCE: 20
gcacattctc atctctgaaa acttccgtgg tttcagagau gagaatgtgc              50

<210> SEQ ID NO 21
<211> LENGTH: 30
<212> TYPE: DNA
<213> ORGANISM: Artificial Sequence
<220> FEATURE:
<223> OTHER INFORMATION: Oligo AGT02028

<400> SEQUENCE: 21

```
ccacggaagt tttcagaatt gagaatgtgc                              30

<210> SEQ ID NO 22
<211> LENGTH: 28
<212> TYPE: DNA
<213> ORGANISM: Artificial Sequence
<220> FEATURE:
<223> OTHER INFORMATION: Oligo AGT02029

<400> SEQUENCE: 22
gcacattctc agatctgaaa ccacggaa                                28

<210> SEQ ID NO 23
<211> LENGTH: 30
<212> TYPE: DNA
<213> ORGANISM: Artificial Sequence
<220> FEATURE:
<223> OTHER INFORMATION: Oligo AGT02039

<400> SEQUENCE: 23
catcaactat caagtgcaaa ccacggaagt                              30

<210> SEQ ID NO 24
<211> LENGTH: 29
<212> TYPE: DNA
<213> ORGANISM: Artificial Sequence
<220> FEATURE:
<223> OTHER INFORMATION: Oligo AGT02040

<400> SEQUENCE: 24
gcacattctc tcatctgaag ctccgtact                               29

<210> SEQ ID NO 25
<211> LENGTH: 30
<212> TYPE: DNA
<213> ORGANISM: Artificial Sequence
<220> FEATURE:
<223> OTHER INFORMATION: Oligo AGT02048

<400> SEQUENCE: 25
gcacattctc agatctgaaa gatcggaagt                              30

<210> SEQ ID NO 26
<211> LENGTH: 30
<212> TYPE: DNA
<213> ORGANISM: Artificial Sequence
<220> FEATURE:
<223> OTHER INFORMATION: Oligo AGT02035

<400> SEQUENCE: 26
gcacattctc agatctgaaa ccacggaagt                              30

<210> SEQ ID NO 27
<211> LENGTH: 22
<212> TYPE: DNA
<213> ORGANISM: Artificial Sequence
<220> FEATURE:
<223> OTHER INFORMATION: Oligo AGT02036

<400> SEQUENCE: 27
gcacattctc agatctgaaa cc                                      22
```

METHODS AND COMPOSITIONS FOR ANALYZING NUCLEOTIDE SEQUENCE MISMATCHES USING RNASE H

FIELD OF THE INVENTION

This invention relates generally to nucleic acid hybridization analysis. More specifically, a method for detecting a point mutation in a DNA strand is provided, which method uses, inter alia, a test nucleic acid strand complementary to a target DNA strand, said nucleic acid strand comprises a sufficient number of ribonucleotide residues that span the position of said point mutation to be detected to form a target DNA strand/test nucleic acid strand duplex and RNase H cleavage of said target DNA strand/test nucleic acid strand duplex. Kits and arrays for detecting a point mutation in a DNA strand comprising test nucleic acid strand comprising a sufficient number of ribonucleotide residues that span the position of said point mutation to be detected are also provided.

BACKGROUND OF THE INVENTION

Nucleic acid hybridization, in the forty years since its discovery, has become a powerful tool with implications for biology, medicine and industry. Hybridization assays are based on the very specific base pairing that is found in hybrids of DNA and RNA. Base sequences of analytical interest appearing along a strand of nucleic acid can be detected very specifically and sensitively by observing the formation of hybrids in the presence of a probe nucleic acid known to comprise a base sequence that is complementary with the sequence of interest. Nucleic acid hybridization has been used for a wide variety of purposes including, for example, identification of specific clones from cDNA and genomic libraries, detecting single base pair polymorphisms in DNA, generating mutations by oligonucleotide mutagenesis, amplifying nucleic acids from single cells or viruses, or detecting microbial infections.

Recent advances in nucleic acid hybridization methods have greatly expanded the scope and extent of its potential applications. Of great interest are approaches to miniaturize hybridization reactions by preparing "microarray biochips" (or "DNA chips") containing large numbers of oligonucleotide probes prepared, for example, through VLSIPS™ technology (See U.S. Pat. Nos. 5,143,854 or 5,561,071). These approaches offer great promise for a wide variety of applications. Microarray biochips are useful for sequencing nucleic acid by hybridization (see, for example, U.S. Pat. No. 5,741,644), for diagnosis of human immunodeficiency virus (see, for example, U.S. Pat. No. 5,861,242) and for screening potential DNA binding drugs (see, for example, U.S. Pat. No. 5,556,752).

When using nucleic acid microarrays, there are two general approaches for detecting hybridization to a nucleic acid. Detection can be accomplished if the target nucleic acid is labeled ("direct labeling approach"). Alternatively, detection can be accomplished by a second probe that is detectably labeled and which can hybridize to the nucleic acid of the sample, which is hybridized to the first probe immobilized on the array ("indirect" labeling approach).

Bagwell, U.S. Pat. No. 5,607,834 discloses a fluorescent probe for binding to a polynucleotide target and methods using such fluorescent probes that comprises: an oligonucleotide having a segment complementary to the polynucleotide target, the oligonucleotide forming two imperfect hairpins both of which together include the segment except for one nucleotide; and one donor fluorophore and one acceptor fluorophore covalently attached to the oligonucleotide so that only when the imperfect hairpins are formed, the donor fluorophore and the acceptor fluorophore are in close proximity to allow resonance energy transfer therebetween. The fluorescent probes disclosed in Bagwell must contain "imperfect hairpins," i.e., containing mismatches in the double-stranded stem segment. In addition, Bagwell does not disclose or teach any immobilized arrays of oligonucleotide probes.

Nazarenko et al., U.S. Pat. No. 5,866,336 disclose an oligonucleotide containing a hairpin structure for use as a primer in detecting a target nucleotide sequence. Similar probes are described in Mergny et al., *Nucleic Acids Res.*, 22:920–928 (1994). Blok and Kramer, *Molecular and Cellular Probes,* 11: 187–194 (1997) describe an amplification RNA probe containing a molecular switch, i.e., a plurality of hairpin structures. Fujiwara and Oishi, *Nucleic Acids Res.,* 26:5728–5733 (1998) describe a method of covalent attachment of probe DNA to double-stranded target DNA where an imperfect hairpin was used to hybridize to a target DNA. Sriprakash and Hartas, *Gene Anal. Techn.,* 6:29–32 (1989) describe a method of generating radioisotope labeled probe with hairpin nucleic acid structure. One common feature of the hairpin structure-containing probes described in the above references is that the nucleotide sequence complementary to a target nucleotide sequence always resides in the single-stranded, not double-stranded, segment of the hairpin structure.

Berkower et al., *J. Biol. Chem.,* 248(17):5914–21 (1973) describe isolation and characterization of an endonuclease, i.e., RNase H, from *Escherichia coli* specific for ribonucleic acid in ribonucleic acid-deoxyribonucleic acid hybrid structures. Donis-Keller, *Nucleic Acids Res.,* 7(1):179–92 (1979) disclose that the hybridization of a DNA oligonucleotide (a specific tetramer or longer) will direct a cleavage by RNase H (EC 3.1.4.34) to a specific site in RNA. The resulting fragments can then be labeled at their 5' or 3' ends, purified, and sequenced directly. This procedure is demonstrated with two RNA molecules of known sequence: 5.8S rRNA from yeast (158 nucleotides) and satellite tobacco necrosis virus (STNV) RNA (1240 nucleotides).

The direct labeling approach can be problematic because nucleic acid labeling methods may fail to label different nucleic acids in a mixture equally. In addition, direct labeling may introduce mutations or other chemical modifications of the sample nucleic acid that prohibit or reduce hybridization.

Detection of hybridization in a microarray biochip by indirect labeling also can be problematic because background hybridization between the second probe may hybridize to the first probe immobilized on the microarray, giving rise to a high false-positive assay background. If the microarray utilizes only a single probe or very limited set of probes, the background may be reduced in the indirect labeling format by designing the specific second probe such that it does not hybridize to the immobilized probes on the array. However, when the microarray contains a wide variety of probe sequences for simultaneously detecting a variety of different nucleic acid targets (the reason for miniaturizing hybridization), designing second probes that are specific and that can avoid background hybridization to the immobilized probes becomes extremely difficult, if not impossible. Accordingly, a need exists for improved hybridization in general and for detecting hybridization and point mutation on microarray formats in particular. The present invention addresses this and other related needs in the art.

SUMMARY OF THE INVENTION

In one aspect, the present invention provides a method for detecting a point mutation in a DNA strand, which method comprises: a) hybridizing a target DNA strand containing or suspected of containing a point mutation with a test nucleic acid strand complementary to said DNA strand to form a target DNA strand/test nucleic acid strand duplex, said nucleic acid strand comprising a sufficient number of ribonucleotide residues to span the position of said point mutation to be detected; b) contacting said target DNA strand/test nucleic acid strand duplex formed in step a) with an RNase H; and c) determining whether said ribonucleotide residues within said test nucleic acid strand are cleaved by said RNase H, wherein said ribonucleotide residues within said test nucleic acid strand are cleaved by said RNase H in the absence of mismatch at said position of said point mutation and said ribonucleotide residues within said test nucleic acid strand are not cleaved by said RNase H in the presence of mismatch at said position of said point mutation and the presence or absence of a point mutation in said target DNA is assessed.

Any suitable nucleic acid strand comprising a sufficient number of ribonucleotide residues that span the position of said point mutation to be detected can be used in the present methods. The test nucleic acid strand can comprise ribonucleotide residues only. Alternatively, the test nucleic acid strand can comprise both ribonucleotide residues and deoxyribonucleotide residues. The test nucleic acid strand can also comprise ribonucleotide residues, deoxyribonucleotide residues and peptide bonds or linkages. In a specific embodiment, the test nucleic acid strand comprises ribonucleotide residues, deoxyribonucleotide residues and peptide bonds or linkages beyond the sufficient number of ribonucleotide residues that span the position of said point mutation to be detected.

Any suitable nucleic acid strand, whether linear and/or circular, can be used in the present methods. In a specific embodiment, the test nucleic acid strand is a part of a hairpin probe having a loop and a stem regions, wherein the loop region has more than 2 nucleotide residues and the target DNA strand and the test nucleic acid strand are hybridized under conditions that favor intermolecular hybridization between the target DNA strand and the test nucleic acid strand over intramolecular hybridization of the test nucleic acid strand itself. The sufficient number of ribonucleotide residues that span the position of said point mutation to be detected can be located within the loop or stem region of the hairpin probe. Preferably, the sufficient number of ribonucleotide residues that span the position of said point mutation to be detected is located within the loop and stem regions of the hairpin probe.

The hairpin probe can further comprise an element or a modification that facilitates intramolecular crosslinking of the test nucleic acid strand upon suitable treatment. The element can be a chemically or photoactively activatable crosslinking agent, e.g., a furocoumarin. The element can also be a macromolecule having multiple ligand binding sites, e.g., a component of biotin-avidin binding system.

When hairpin probes are used in the present method, the conditions that favor intermolecular hybridization between the target DNA strand and the test nucleic acid strand over intramolecular hybridization of the test nucleic acid strand itself can be achieved by any suitable methods, e.g., by controlling compositions of the target DNA strand and the test nucleic acid strand so that the Tm of the intermolecular hybrid is higher than the Tm of the intramolecular hybrid. Preferably, the Tm of the intermolecular hybrid is at least 2° C. higher than the Tm of the intramolecular hybrid.

In a preferred embodiment, the sufficient number of ribonucleotide residues within the test nucleic acid strand can comprise at least a ribonucleotide sequence having the formula 5'-RXR-3', 5'-RRX-3' or 5'-RRXR-3', or a complementary strand thereof, wherein R is an ribonucleotide residue complementary to its corresponding deoxyribonucleotide in said target DNA strand and X represents the position of said point mutation to be detected and X is a ribonucleotide residue that is complementary or not complementary to its corresponding deoxyribonucleotide in said target DNA strand. In a specific embodiment, X in the above formulas can be complementary to the corresponding deoxyribonucleotide that would be present in a wild-type target DNA strand and cleavage of the ribonucleotide residues within the test nucleic acid strand indicates the absence of a point mutation at position X and failure of the cleavage of the ribonucleotide residues within the test nucleic acid strand indicates the presence of a point mutation at position X. In another specific embodiment, X is not complementary to the corresponding deoxyribonucleotide that would be present in a wild-type target DNA strand and the cleavage of the ribonucleotide residues within the test nucleic acid strand indicates the presence of a point mutation at position X.

The cleavage of the ribonucleotide residues by RNase H can be assessed by suitable methods. For example, the cleavage of the ribonucleotide residues can be assessed by analyzing the disappearance of the target DNA strand/test nucleic acid strand duplex, e.g., by gel electrophoresis. Any type of gel electrophoresis, including agarose gel electrophoresis, pulsed-field gel electrophoresis, capillary electrophoresis and polyacrylamide gel electrophoresis, can be used (See generally, Ausubel (Ed.) *Current Protocols in Molecular Biology*, 2. *Preparation and Analysis of DNA* and 4. *Preparation and Analysis of RNA*, John Wiley & Sons, Inc. (2000)). Other suitable analytical methods such as mass spectrometry, chromatograph, filtration and centrifugation can also be used. In a preferred embodiment, each of the target DNA strand and the test nucleic acid strand contains an element, whereby the formation of the target DNA strand/test nucleic acid strand duplex brings the two elements into close proximity to generate a detectable signal, and the cleavage of the ribonucleotide residues disrupts or interferes with the close proximity of the two elements and alters the detectable signal. More preferably, the elements belong to a enzyme/substrate pair or are components of a fluorescence resonance energy transfer (FRET) system.

The present method can be conducted in a liquid or solution. Alternatively, the present method can be conducted on a surface, e.g., by using a test nucleic acid strand that is immobilized on a solid support.

The present method can be conducted to detect a single point mutation at a time. Preferably, the present method can be conducted in high throughput mode, i.e., by analyzing a plurality of point mutations simultaneously. For example, a plurality of the test nucleic acid strands immobilized on a solid support can be used. Preferably, each of the plurality of the test nucleic acid strands is capable of detecting a different point mutation. More preferably, a plurality of samples is assayed simultaneously using a plurality of the test nucleic acid strands, either in a liquid or solution, or on a surface, wherein each of the plurality of the test nucleic acid strands is capable of detecting a different point mutation.

In another aspect, the present invention provides a kit for detecting a point mutation in a DNA strand, which kit comprises: a) a test nucleic acid strand that is complementary to a target DNA strand containing or suspected of containing a point mutation to be detected and capable of forming a target DNA strand/test nucleic acid strand duplex, said test nucleic acid strand comprising a sufficient number of ribonucleotide residues to span the position of said point mutation to be detected; and b) an RNase H.

In still another aspect, the present invention provides an array of test nucleic acid strands immobilized on a solid support for detecting a point mutation in a DNA strand, comprising a solid support suitable for use in nucleic acid hybridization having immobilized thereon a plurality of test nucleic acid strands, at least one of the test nucleic acid strands comprising a sufficient number of ribonucleotide residues to span the position of said point mutation to be detected to form a target DNA strand/test nucleic acid strand duplex.

BRIEF DESCRIPTION OF THE DRAWINGS

FIG. 3 shows the minimum number of ribonucleotides in DNA/RNA chimeric oligonucleotide for RNase H cleavage. The positions of the oligo alone and the duplex are indicated, respectively (SEQ ID NOS:8–12). 3A. Lane 1: AGT02008+AGT02009 without RNase H treatment; Lane 2: AGT02008+AGT02009 with RNase H treatment; Lane 3: AGT02012+AGT02009 without RNase H treatment; Lane 4: AGT02012+AGT02009 with RNase H treatment; Lane 5: AGT02013+AGT02009 without RNase H treatment; Lane 6: AGT02013+AGT02009 with RNase H treatment; Lane 7: AGT02014+AGT02009 without RNase H treatment; and Lane 8: AGT02014+AGT02009 with RNase H treatment. 3B. Lane 1: AGT02008 without RNase H treatment; Lane 2: AGT02008 with RNase H treatment (5 units, 1 hour); Lane 3: AGT02012 without RNase H treatment; Lane 4: AGT02012 with RNase H treatment (5 units, 1 hour); Lane 5: AGT02012 with RNase H treatment (10 units, 1 hour); Lane 6: AGT02012 with RNase H treatment (50 units, 1 hour); Lane 7: AGT02013 without RNase H treatment; Lane 8: AGT02013 with RNase H treatment (5 units, 1 hour); Lane 9: AGT02013 with RNase H treatment (10 units, 1 hour); Lane 10: AGT02013 with RNase H treatment (50 units, 1 hour).

FIG. 4 shows that mismatch inhibits RNase H activity. The positions of the oligo alone and the duplex are indicated, respectively (SEQ ID NOS:8, 12–18). 4A. Lane 1: AGT02009 without RNase H treatment; Lane 2: AGT02008+AGT02009 without RNase H treatment; Lane 3: AGT02008+AGT02009 with RNase H treatment; Lane 4: AGT02020 without RNase H treatment; Lane 5: AGT02008+AGT02020 without RNase H treatment; Lane 6: AGT02008+AGT02020 with RNase H treatment; Lane 7: AGT02021 without RNase H treatment; Lane 8: AGT02008+AGT02021 without RNase H treatment; Lane 9: AGT02008+AGT02021 with RNase H treatment; Lane 10: AGT02022 without RNase H treatment; Lane 11: AGT02008+AGT02022 without RNase H treatment; Lane 12: AGT02008+AGT02022 with RNase H treatment; Lane 13: AGT02023 without RNase H treatment; Lane 14: AGT02008+AGT02023 without RNase H treatment; Lane 15: AGT02008+AGT02023 with RNase H treatment. 4B. Lane 1: AGT02008+AGT02009 without RNase H treatment; Lane 2: AGT02008+AGT02009 with RNase H treatment; Lane 3: AGT02008+AGT02021 without RNase H treatment; Lane 4: AGT02008+AGT02021 with RNase H treatment; Lane 5: AGT02008+AGT02024 without RNase H treatment; Lane 6: AGT02008+AGT02024 with RNase H treatment; Lane 7: AGT02008+AGT02025 without RNase H treatment; Lane 8: AGT02008+AGT02025 with RNase H treatment.

FIG. 5 shows that RNase H can be used in hairpin structure cleavage assay. The positions of the hairpin oligo, the cut out form of the hairpin oligo, the uncut duplex and the target DNA are indicated, respectively (SEQ ID NOS: 19–22). 5A. Lane 1: AGT02010 without RNase H treatment; Lane 2: AGT02010 with RNase H treatment; Lane 3: AGT02010+AGT02028 with RNase H treatment (annealing temperature at 60.2° C.); Lane 4: AGT02010+AGT02028 with RNase H treatment (annealing temperature at 64.5° C.); Lane 5: AGT02010+AGT02028 with RNase H treatment (annealing temperature at 69.6° C.); Lane 6: AGT02010+AGT02028 with RNase H treatment (annealing temperature at 74.8° C.); Lane 7: AGT02010+AGT02028 with RNase H treatment (annealing temperature at 79.9° C.); Lane 8: AGT02010+AGT02028 without RNase H treatment (annealing temperature at 79.9° C.). 5B. Lane 1: AGT02011 without RNase H treatment; Lane 2: AGT02011 with RNase H treatment; Lane 3: AGT02011+AGT02029 with RNase H treatment (annealing temperature at 60.2° C.); Lane 4: AGT02011+AGT02029 with RNase H treatment (annealing temperature at 64.5° C.); Lane 5: AGT02011+AGT02029 with RNase H treatment (annealing temperature at 69.6° C.); Lane 6: AGT02011+AGT02029 with RNase H treatment (annealing temperature at 74.8° C.); Lane 7: AGT02011+AGT02029 with RNase H treatment (annealing temperature at 79.9° C.); Lane 8: AGT02011+AGT02029 without RNase H treatment (annealing temperature at 79.9° C.).

FIG. 6 shows that the hairpin probe can bind with single strand target oligo at a wide range of temperatures. The positions of the duplex, the hairpin oligo and the target DNA are indicated, respectively (SEQ ID NOS:19,21). 6A. Lane 1: AGT02010; Lane 2: AGT02028; Lane 3: AGT02010+AGT02028 (annealing temperature at 37° C.); Lane 4: AGT02010+AGT02028 (annealing temperature at 47° C.); Lane 5: AGT02010+AGT02028 (annealing temperature at 55° C.); Lane 6: AGT02010+AGT02028 (annealing temperature at 65° C.); Lane 7: AGT02010+AGT02028 (annealing temperature at 75° C.); Lane 8: AGT02010+AGT02028 (annealing temperature at 85° C.). 6B. Lane 1: AGT02010; Lane 2: AGT02028; Lane 3: AGT02010+

AGT02028 (0.25 μg) (annealing temperature at 18° C.); Lane 4: AGT02010+AGT02028 (3 μg) (annealing temperature at 18° C.); Lane 5: AGT02010+AGT02028 (0.25 μg) (annealing temperature at 25° C.); Lane 6: AGT02010+ AGT02028 (3 μg) (annealing temperature at 25° C.); Lane 7: AGT02010+AGT02028 (0.25 μg) (annealing temperature at 30° C.); Lane 8: AGT02010+AGT02028 (3 μg) (annealing temperature at 30° C.). 6C. Lane 1: AGT02010; Lane 2: AGT02028; Lane 3: AGT02010+AGT02028 (annealing at room temperature for 1 minute); Lane 4: AGT02010+AGT02028 (annealing at room temperature for 2 minutes); Lane 5: AGT02010+AGT02028 (annealing at room temperature for 3 minutes); Lane 6: AGT02010+ AGT02028 (annealing at room temperature for 4 minutes); Lane 7: AGT02010+AGT02028 (annealing at room temperature for 5 minutes); Lane 8: AGT02010+AGT02028 (annealing at 4° C. for 10 minutes).

Figure 1:
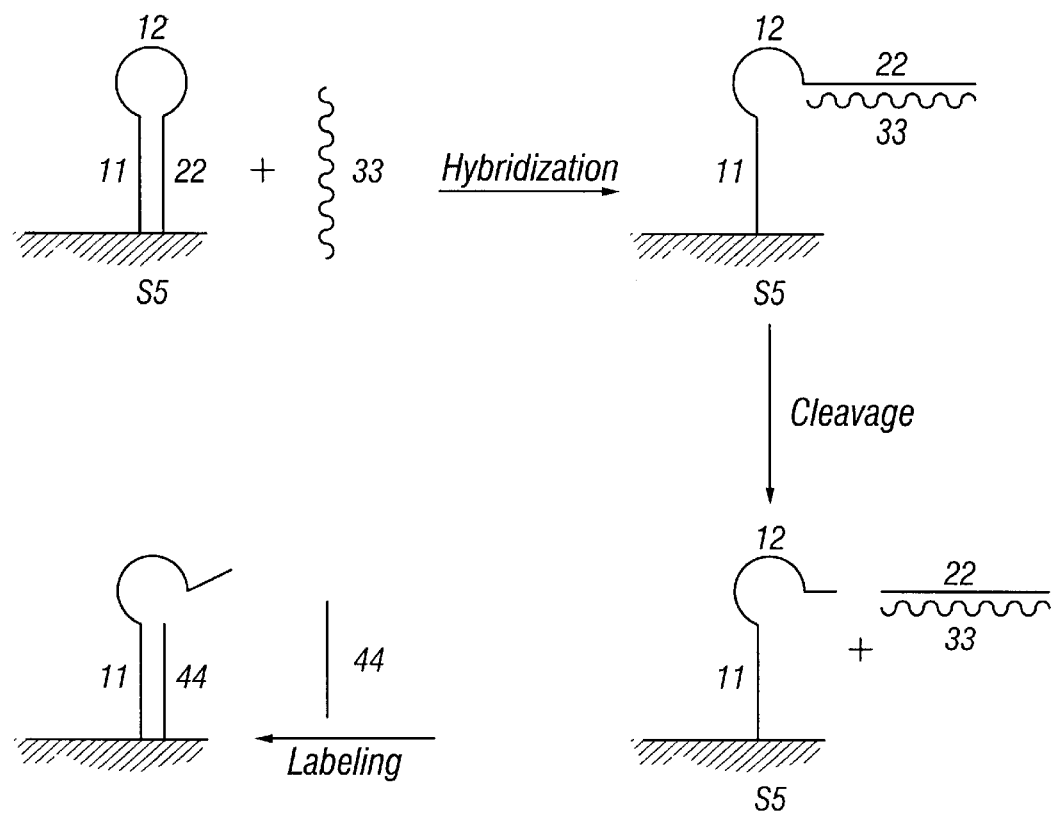
FIG. 1 illustrates one embodiment of nucleic acid hybridization analysis using an immobilized hairpin probe. SS depicts a solid support upon which the hairpin probe is immobilized. 11, 12, 22 are parts of an immobilized hairpin probe, wherein 11 and 22 forms the double-stranded stem region, 12 is the single-stranded loop region, which can be a non-nucleic acid moiety, and at least a portion of 22 is complementary to the target nucleotide sequence 33. Under suitable conditions, 22 forms a duplex with the target nucleotide sequence 33 and leaves 11 as a single-stranded region. The duplex formed between 22 and 33 is then cleaved off the immobilized probe, preferably with an enzyme, e.g., a RNase H or a restriction enzyme that recognizes a restriction enzyme cleavage site within the duplex. A labeled detecting probe, 44, is hybridized with the single-stranded region 11, which gives a readout signal for detecting hybridization between the hairpin probe and the target nucleotide sequence. If, in the original hybridization step, 22 and 33 are not complementary to each other and do not form a duplex, 11 is still masked by 22 and cannot be hybridized with the detecting probe 44, so no signal is detected.
Figure 2:
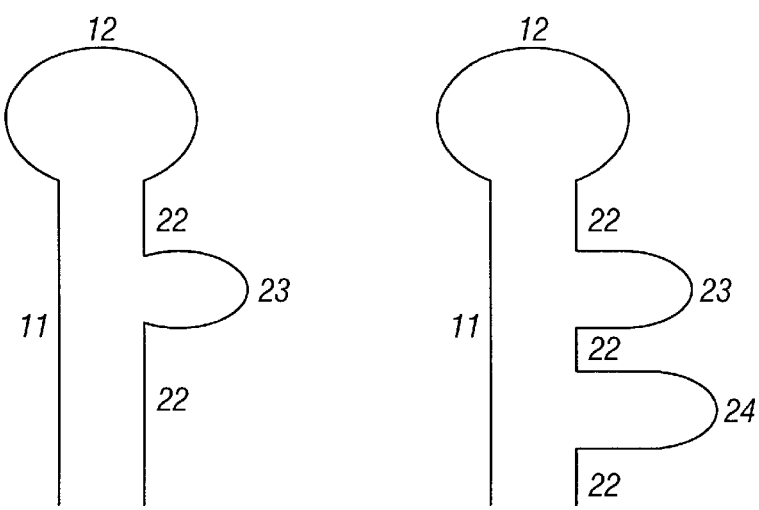
FIG. 2 illustrates hairpin probes with multiple single-stranded loop regions. 22, 23 and 24 are complementary to target nucleotide sequence. 12, 23 and 24 can be non-nucleic acid moieties, e.g., linked polyethylene glycols.
Figure 7:
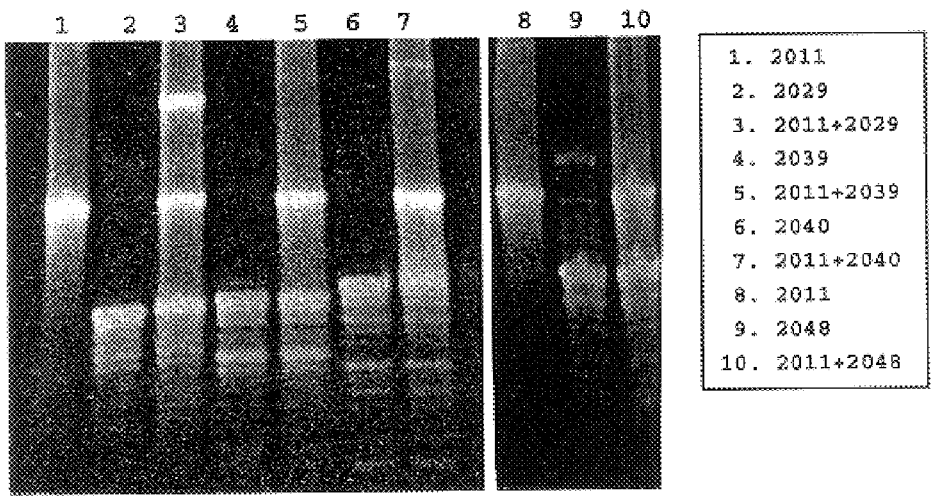

FIG. 7 shows the sequence specificity of hairpin probe. The positions of the duplex, the hairpin oligo and the target DNA are indicated, respectively (SEQ ID NOS:20, 22–25). Lane 1: AGT02011; Lane 2: AGT02029; Lane 3: AGT02011+AGT02029; Lane 4: AGT02039; Lane 5: AGT02011+AGT02039; Lane 6: AGT02040; Lane 7: AGT02011+AGT02040; Lane 8: AGT02011; Lane 9: AGT02048; Lane 10: AGT02011+AGT02048.

Figure 8:
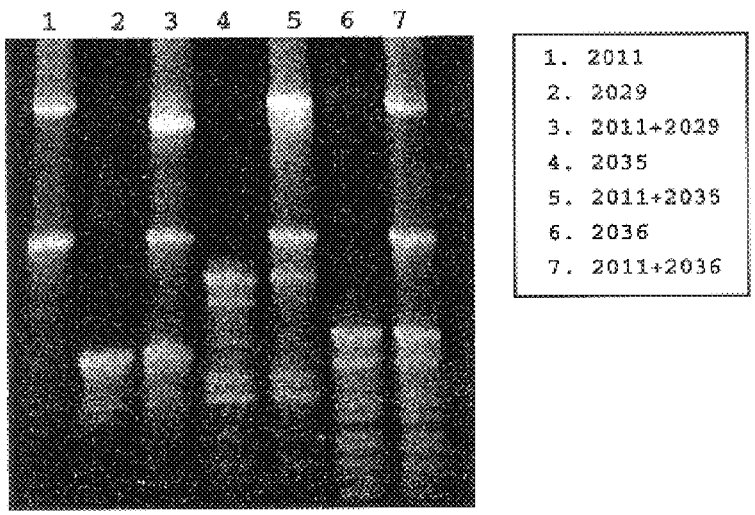

FIG. 8 shows that the loop region of a hairpin probe play an important role in target sequence binding. The positions of the duplex, the hairpin oligo and the target DNA are indicated, respectively (SEQ ID NOS:20, 22, 26, 27). Lane 1: AGT02011; Lane 2: AGT02029; Lane 3: AGT02011+ AGT02029; Lane 4: AGT02035; Lane 5: AGT02011+ AGT02035; Lane 6: AGT02036; Lane 7: AGT02011+ AGT02036.

DETAILED DESCRIPTION OF THE INVENTION

The present invention provides methods, kits and arrays for detecting a point mutation in a DNA strand using a test nucleic acid strand comprising a sufficient number of ribonucleotide residues that span the position of said point mutation to be detected in combination with RNase H cleavage. For clarity of disclosure, and not by way of limitation, the detailed description of the invention is divided into the subsections that follow.

A. Definitions

Unless defined otherwise, all technical and scientific terms used herein have the same meaning as is commonly understood by one of ordinary skill in the art to which this invention belongs. All patents, applications, published applications and other publications and sequences from GenBank and other databases referred to herein are incorporated by reference in their entirety. If a definition set forth in this section is contrary to or otherwise inconsistent with a definition set forth in applications, published applications and other publications and sequences from GenBank and other data bases that are herein incorporated by reference, the definition set forth in this section prevails over the definition that is incorporated herein by reference.

As used herein, "a" or "an" means "at least one" or "one or more."

As used herein, "base-pairing" refers to the specific hydrogen bonding between purines and pyrimidines in double-stranded nucleic acids. In DNA, the pairs are adenine (A) and thymine (T), and guanine (G) and cytosine (C), while in RNA they are adenine (A) and uracil (U), and guanine (G) and cytosine (C). Base-pairing leads to the formation of a nucleic acid double helix from two complementary single strands.

As used herein, "point mutation" refers to a base-pair mismatch, i.e., any base-pairing other than any of the normal A:T(U) and C:G pairs. Non-limiting examples of base-pair mismatch include A:A, A:C, A:G, C:C, C:T, G:G, G:T, T:T, C:U, G:U, T:U, U:U, 5-formyluracil (fU):G, 7,8-dihydro-8-oxo-guanine (8-oxoG):C, 8-oxoG:A.

As used herein, "said nucleic acid strand comprises a sufficient number of ribonucleotide residues that span the position of said point mutation to be detected" means that the test nucleic acid strand comprises, in the region that spans the position of the point mutation to be detected, a minimal number of ribonucleotide residues in an appropriate orientation (polarity) so that, without a point mutation at the position X, the ribonucleotide residues in the test nucleic acid strand/target DNA strand can be cleaved by RNase H and that, the presence of a point mutation at the position X will block the RNase H cleavage.

As used herein, "RNase H" refers to a ribonuclease that specifically hydrolyzes the phosphodiester bonds of RNA:DNA complexes to generate products with 3' hydroxyl and 5' phosphate ends. RNase H will not degrade single stranded or double-stranded DNA or RNA. RNase H cleavage can be directed to specific sites by hybridizing short deoxyoligonucleotides to the RNA. As used herein, RNase H encompasses enzymes in which the sole activity is to specifically hydrolyzes the phosphodiester bonds of RNA:DNA complexes and enzymes, and in which such cleavage activity is one of their several enzymatic activities, e.g., reverse transcriptase. It is intended that RNase H encompasses enzymes with conservative amino acid substitutions that do not substantially alter its cleavage activity. Suitable conservative substitutions of amino acids are known to those of skill in this art and may be made generally without altering the biological activity of the resulting molecule. Those of skill in this art recognize that, in general, single amino acid substitutions in non-essential regions of a polypeptide do not substantially alter biological activity (see, e.g., Watson et al. *Molecular Biology of the Gene,* 4th Edition, 1987, The Bejacmin/Cummings Pub. co., p.224).

As used herein, "locus" refers to the site in linkage map or on a chromosome where the nucleic acid sequence, e.g., gene, for a particular trait is located. Any one of the alleles of a sequence may be present at this site.

As used herein, "an allele" refers to one of any different forms or variants of a gene found at the same place, or a locus, on a chromosome.

As used herein, "polymorphism" refers to the existence, in a population, of two or more alleles of a nucleic acid sequence, e.g., gene, where the frequency of the rarer alleles is greater than can be explained by recurrent mutation alone (typically greater than 1%).

As used herein, "single nucleotide polymorphism ("SNP")" refers to polymorphisms arising from the replacement of only a single nucleotide from the initially present gene sequence.

As used herein, "sample" refers to anything which may contain an analyte for which an analyte assay is desired. The sample may be a biological sample, such as a biological fluid or a biological tissue. Examples of biological fluids include urine, blood, plasma, serum, saliva, semen, stool, sputum, cerebral spinal fluid, tears, mucus, amniotic fluid or the like. Biological tissues are aggregates of cells, usually of a particular kind together with their intercellular substance that form one of the structural materials of a human, animal, plant, bacterial, fungal or viral structure, including connective, epithelium, muscle and nerve tissues. Examples of biological tissues also include organs, tumors, lymph nodes, arteries and individual cell(s).

As used herein, "hairpin structure" refers to a polynucleotide or nucleic acid that contains a double-stranded stem segment and a single-stranded loop segment wherein the two polynucleotide or nucleic acid strands that form the double-stranded stem segment are linked and separated by the single polynucleotide or nucleic acid strand that forms the loop segment. The "hairpin structure" can also further comprise 3' and/or 5' single-stranded region(s) extending from the double-stranded stem segment.

As used herein, "conditions that favor intermolecular hybridization between the target DNA strand and the test nucleic acid strand over intramolecular hybridization of the test nucleic acid strand itself" refers to the conditions under which the intermolecular hybrid can stably exist and be detected while the intramolecular hybrid cannot stably exist and be detected.

As used herein, "melting temperature" ("Tm") refers to the midpoint of the temperature range over which nucleic acid duplex, i.e., DNA:DNA, DNA:RNA and RNA:RNA, is denatured.

As used herein: "stringency of hybridization" in determining percentage mismatch is as follows:

1) high stringency: 0.1× SSPE, 0.1% SDS, 65° C.;
2) medium stringency: 0.2× SSPE, 0.1% SDS, 50° C. (also referred to as moderate stringency); and
3) low stringency: 1.0× SSPE, 0.1% SDS, 50° C.

It is understood that equivalent stringencies may be achieved using alternative buffers, salts and temperatures (See generally, Ausubel (Ed.) *Current Protocols in Molecular Biology*, 2.9A. *Southern Blotting*, 2.9B. *Dot and Slot Blotting of DNA* and 2.10. *Hybridization Analysis of DNA Blots*, John Wiley & Sons, Inc. (2000)).

As used herein, "assessing" refers to quantitative and/or qualitative determination of the RNase H cleavage of the ribonucleotide residues within the test nucleic acid strand, e.g., obtaining an absolute value for the amount or concentration of the disappearance of the target DNA/test nucleic acid strand duplex and/or the formation of cleavage product(s), and also of obtaining an index, ratio, percentage, visual or other value indicative of the level of the RNase H cleavage. Assessment may be direct or indirect and the chemical species actually detected need not of course be the duplex or cleavage product itself but may, for example, be a derivative thereof or some further substance.

As used herein, "plant" refers to any of various photosynthetic, eucaryotic multi-cellular organisms of the kingdom Plantae, characteristically producing embryos, containing chloroplasts, having cellulose cell walls and lacking locomotion.

As used herein, "animal" refers to a multi-cellular organism of the kingdom of Animalia, characterized by a capacity for locomotion, nonphotosynthetic metabolism, pronounced response to stimuli, restricted growth and fixed bodily structure. Non-limiting examples of animals include birds such as chickens, vertebrates such fish and mammals such as mice, rats, rabbits, cats, dogs, pigs, cows, ox, sheep, goats, horses, monkeys and other non-human primates.

As used herein, "tissue" refers to a collection of similar cells and the intracellular substances surrounding them. There are four basic tissues in the body: 1) epithelium; 2) connective tissues, including blood, bone, and cartilage; 3) muscle tissue; and 4) nerve tissue.

As used herein, "organ" refers to any part of the body exercising a specific function, as of respiration, secretion or digestion.

As used herein, "disease or disorder" refers to a pathological condition in an organism resulting from, e.g., infection or genetic defect, and characterized by identifiable symptoms.

As used herein, "neoplasm (neoplasia)" refers to abnormal new growth, and thus means the same as tumor, which may be benign or malignant. Unlike hyperplasia, neoplastic proliferation persists even in the absence of the original stimulus.

As used herein, "cancer" refers to a general term for diseases caused by any type of malignant tumor.

As used herein, "an immune system disease or disorder" refers to a pathological condition caused by a defect in the immune system. The immune system is a complex and highly developed system, yet its mission is simple: to seek and kill invaders. If a person is born with a severely defective immune system, death from infection by a virus, bacterium, fungus or parasite will occur. In severe combined immunodeficiency, lack of an enzyme means that toxic waste builds up inside immune system cells, killing them and thus devastating the immune system. A lack of immune system cells is also the basis for DiGeorge syndrome: improper development of the thymus gland means that T cell production is diminished. Most other immune disorders result from either an excessive immune response or an 'autoimmune attack'. For example, asthma, familial Mediterranean fever and Crohn disease (inflammatory bowel disease) all result from an over-reaction of the immune system, while autoimmune polyglandular syndrome and some facets of diabetes are due to the immune system attacking 'self' cells and molecules. A key part of the immune system's role is to differentiate between invaders and the body's own cells—when it fails to make this distinction, a reaction against 'self' cells and molecules causes autoimmune disease.

As used herein, "a metabolism disease or disorder" refers to a pathological condition caused by errors in metabolic processes. Metabolism is the means by which the body derives energy and synthesizes the other molecules it needs from the fats, carbohydrates and proteins we eat as food, by enzymatic reactions helped by minerals and vitamins. There is a significant level of tolerance of errors in the system: often, a mutation in one enzyme does not mean that the individual will suffer from a disease. A number of different enzymes may compete to modify the same molecule, and there may be more than one way to achieve the same end result for a variety of metabolic intermediates. Disease will only occur if a critical enzyme is disabled, or if a control mechanism for a metabolic pathway is affected.

As used herein, "a muscle and bone disease or disorder" refers to a pathological condition caused by defects in genes important for the formation and function of muscles, and connective tissues. Connective tissue is used herein as a broad term that includes bones, cartilage and tendons. For example, defects in fibrillin—a connective tissue protein that is important in making the tissue strong yet flexible—cause Marfan syndrome, while diastrophic dysplasia is caused by a defect in a sulfate transporter found in cartilage. Two diseases that originate through a defect in the muscle cells themselves are Duchenne muscular dystrophy (DMD) and myotonic dystrophy (DM). DM is another 'dynamic mutation' disease, similar to Huntington disease, that involves the expansion of a nucleotide repeat, this time in a muscle protein kinase gene. DMD involves a defect in the cytoskeletal protein, dystrophin, which is important for maintaining cell structure.

As used herein, "a nervous system disease or disorder" refers to a pathological condition caused by defects in the nervous system including the central nervous system, i.e., brain, and the peripheral nervous system. The brain and nervous system form an intricate network of electrical signals that are responsible for coordinating muscles, the senses, speech, memories, thought and emotion. Several diseases that directly affect the nervous system have a genetic component: some are due to a mutation in a single gene, others are proving to have a more complex mode of inheritance. As our understanding of the pathogenesis of neurodegenerative disorders deepens, common themes begin to emerge: Alzheimer brain plaques and the inclusion bodies found in Parkinson disease contain at least one common component, while Huntington disease, fragile X syndrome and spinocerebellar atrophy are all 'dynamic mutation' diseases in which there is an expansion of a DNA repeat sequence. Apoptosis is emerging as one of the molecular mechanisms invoked in several neurodegenerative diseases, as are other, specific, intracellular signaling events. The biosynthesis of myelin and the regulation of cholesterol traffic also figure in Charcot-Marie-Tooth and Neimann-Pick disease, respectively.

As used herein, "a signal disease or disorder" refers to a pathological condition caused by defects in the signal transduction process. Signal transduction within and between cells mean that they can communicate important information and act upon it. Hormones released from their site of synthesis carry a message to their target site, as in the case of leptin, which is released from adipose tissue (fat cells) and transported via the blood to the brain. Here, the leptin signals that enough has been eaten. Leptin binds to a receptor on the surface of hypothalamus cells, triggering subsequent intracellular signaling networks. Intracellular signaling defects account for several diseases, including cancers, ataxia telangiectasia and Cockayne syndrome. Faulty DNA repair mechanisms are also invoked in pathogenesis, since control of cell division, DNA synthesis and DNA repair all are inextricably linked. The end-result of many cell signals is to alter the expression of genes (transcription) by acting on DNA-binding proteins. Some diseases are the result of a lack of or a mutation in these proteins, which stop them from binding DNA in the normal way. Since signaling networks impinge on so many aspects of normal function, it is not surprising that so many diseases have at least some basis in a signaling defect.

As used herein, "a transporter disease or disorder" refers to a pathological condition caused by defects in a transporter, channel or pump. Transporters, channels or pumps that reside in cell membranes are key to maintaining the right balance of ions in cells, and are vital for transmitting signals from nerves to tissues. The consequences of defects in ion channels and transporters are diverse, depending on where they are located and what their cargo is. For example, in the heart, defects in potassium channels do not allow proper transmission of electrical impulses, resulting in the arrhythmia seen in long QT syndrome. In the lungs, failure of a sodium and chloride transporter found in epithelial cells leads to the congestion of cystic fibrosis, while one of the most common inherited forms of deafness, Pendred syndrome, looks to be associated with a defect in a sulphate transporter.

As used herein, "infection" refers to invasion of the body of a multi-cellular organism with organisms that have the potential to cause disease.

As used herein, "infectious organism" refers to an organism that is capable to cause infection of a multi-cellular organism. Most infectious organisms are microorganisms such as viruses, bacteria and fungi.

As used herein, "bacteria" refers to small prokaryotic organisms (linear dimensions of around 1 $\mu$m) with non-compartmentalized circular DNA and ribosomes of about 70S. Bacteria protein synthesis differs from that of eukaryotes. Many anti-bacterial antibiotics interfere with bacteria proteins synthesis but do not affect the infected host.

As used herein, "eubacteria" refers to a major subdivision of the bacteria except the archaebacteria. Most Gram-positive bacteria, cyanobacteria, mycoplasmas, enterobacteria, pseudomonas and chloroplasts are eubacteria. The cytoplasmic membrane of eubacteria contains ester-linked lipids; there is peptidoglycan in the cell wall (if present); and no introns have been discovered in eubacteria.

As used herein, "archaebacteria" refers to a major subdivision of the bacteria except the eubacteria. There are 3 main orders of archaebacteria: extreme halophiles, methanogens and sulphur-dependent extreme thermophiles. Archaebacteria differs from eubacteria in ribosomal structure, the possession (in some case) of introns, and other features including membrane composition.

As used herein, "virus" refers to obligate intracellular parasites of living but non-cellular nature, consisting of DNA or RNA and a protein coat. Viruses range in diameter from about 20 to about 300 nm. Class I viruses (Baltimore classification) have a double-stranded DNA as their genome; Class II viruses have a single-stranded DNA as their genome; Class III viruses have a double-stranded RNA as their genome; Class IV viruses have a positive single-stranded RNA as their genome, the genome itself acting as mRNA; Class V viruses have a negative single-stranded RNA as their genome used as a template for mRNA synthesis; and Class VI viruses have a positive single-stranded RNA genome but with a DNA intermediate not only in replication but also in mRNA synthesis. The majority of viruses are recognized by the diseases they cause in plants, animals and prokaryotes. Viruses of prokaryotes are known as bacteriophages.

As used herein, "fungi" refers to a division of eucaryotic organisms that grow in irregular masses, without roots, stems, or leaves, and are devoid of chlorophyll or other pigments capable of photosynthesis. Each organism (thallus) is unicellular to filamentous, and possess branched somatic structures (hyphae) surrounded by cell walls containing glucan or chitin or both, and containing true nuclei.

As used herein, "reverse transcriptase" refers to an enzyme that synthesizes DNA using a RNA as the template. It is intended to encompass any reverse transcriptase with conservative amino acid substitutions that do not substantially alter its activity.

B. Methods for Detecting a Point Mutation in a DNA Strand

In one aspect, the present invention provides a method for detecting a point mutation in a DNA strand, which method comprises: a) hybridizing a target DNA strand containing or suspected of containing a point mutation with a test nucleic acid strand complementary to said DNA strand to form a target DNA strand/test nucleic acid strand duplex, said nucleic acid strand comprising a sufficient number of ribonucleotide residues to span the position of said point mutation to be detected; b) contacting said target DNA strand/test nucleic acid strand duplex formed in step a) with an RNase H; and c) determining whether said ribonucleotide residues within said test nucleic acid strand are cleaved by said RNase H, wherein said ribonucleotide residues within said test nucleic acid strand are cleaved by said RNase H in the absence of mismatch at said position of said point mutation and said ribonucleotide residues within said test nucleic acid strand are not cleaved by said RNase H in the presence of mismatch at said position of said point mutation and the presence or absence of a point mutation in said target DNA is assessed.

Test Nucleic Acid Strand

Any suitable nucleic acid strand comprising a sufficient number of ribonucleotide residues that span the position of said point mutation to be detected can be used in the present methods. The test nucleic acid strand can comprise ribonucleotide residues only. Alternatively, the test nucleic acid strand can comprise both ribonucleotide residues and deoxyribonucleotide residues. The test nucleic acid strand can also comprise ribonucleotide residues, deoxyribonucleotide residues and/or peptide bonds. In a specific embodiment, the test nucleic acid strand comprises ribonucleotide residues, deoxyribonucleotide residues and/or peptide bonds beyond the sufficient number of ribonucleotide residues that span the position of said point mutation to be detected.

Any suitable nucleic acid strand, whether linear and/or circular, can be used in the present methods. In a specific embodiment, the test nucleic acid strand is a part of a hairpin probe having a loop and a stem regions, wherein the loop region has more than 2 nucleotide residues and the target DNA strand and the test nucleic acid strand are hybridized under conditions that favor intermolecular hybridization between the target DNA strand and the test nucleic acid strand over intramolecular hybridization of the test nucleic acid strand itself. The sufficient number of ribonucleotide residues that span the position of said point mutation to be detected can be located within the loop or stem region of the hairpin probe. Also preferably, the sufficient number of ribonucleotide residues that span the position of said point mutation to be detected is located within the loop and stem regions of the hairpin probe.

The test nucleic acid strand can comprise any kind of oligonucleotide or nucleic acid strand(s) containing genetically-coded and/or naturally occurring structures. The test nucleic acid strand, e.g., the linear probes or the hairpin probes used herein, can comprise DNA, RNA, or a combination of DNA and RNA. The linear or hairpin probes also can comprise non-natural elements such as non-natural bases, e.g., inosine and xanthine, non-natural sugars, e.g., 2'-methoxy ribose, or non-natural phosphodiester linkages, e.g., methylphosphonates, phosphorothioates and peptides. For example, in one embodiment of the invention, hairpin probes comprising both DNA and RNA are designed such that DNA of the probe contains a sequence of nucleotides that are complementary to an RNA sequence of the probe running in opposite directions, such that upon intramolecular hybridization, the double stranded portion of the hairpin probe has DNA hybridized to RNA. Alternatively, or in addition, one or both of the complementary sequences of the intramolecularly hybridizing portion of the hairpin probe can be made resistant to a particular nuclease. For example, a methylphosphonate DNA sequence is resistant to cleavage by RNase H. In one specific embodiment, the probe comprises DNA, RNA, PNA or a derivative thereof. In another specific embodiment, the probe comprises both DNA and RNA or derivatives thereof.

The portion of the nucleotide sequences located within the double stranded segment and the single stranded loop can be substantially complementary to its corresponding nucleotide sequence in the target DNA sequence. Preferably, the portion of the nucleotide sequences located within the double stranded segment and the single stranded loop is a perfect match to its corresponding nucleotide sequence in the target DNA sequence.

The single stranded loop of the probe must contain more than 2 nucleotides. For example, The single stranded loop of the probe can comprise at least 3, 4, 5, 6, 7, 8, 9, 10, 15 or more nucleotides.

The double stranded segment of the hairpin structure can be formed between two perfectly matched nucleotide sequences or two substantially matched nucleotide sequences.

The probe can further comprise an element or a modification that facilitates intramolecular crosslinking of the probe upon suitable treatment. Such an element can be a chemically or photoactively activatable crosslinking agent, e.g., furocoumarins. Alternatively, such element can be a macromolecule having multiple ligand binding sites, e.g., component(s) of biotin-avidin binding system or an antigen-antibody binding system.

The probe can further comprise an element or a modification that renders the probe sensitive or resistant to nuclease digestion. For example, such an element can be a restriction enzyme cleavage site. In another example, at least a portion of the double stranded segment of the probe is a duplex between a DNA strand and a RNA strand, said DNA strand contains methylphosphonates and at least a portion of said RNA strand is complementary to a target DNA sequence spanning the point mutation to be detected. The methylphosphonate DNA:RNA hybrid in the probe itself is resistant to RNase H cleavage. However, once the probe hybridizes with a target DNA sequence, the RNA strand in the formed RNA:DNA duplex can be cleaved with RNase H treatment.

Probe sequences that are designed to hybridize intramolecularly or intermolecularly should be sufficiently complementary to hybridize under the selected conditions. Sufficient complementarity exists when an RNA or DNA strand will hybridize under selective hybridization conditions to its complement. Typically, selective hybridization will occur when there is at least about 65% complementarity over a stretch of at least 14 to 25 nucleotides, preferably at least about 75%, more preferably at least about 90% complementarity (See e.g., Kanehisa, *Nucleic Acids Res.,* 12:203 (1984)).

The intramolecular hybridization sequences in the hairpin probe can be separated by a flexible linker essentially as described in U.S. Pat. No. 5,556,752 to Lockhart et al. Briefly, the flexible linker is chosen to be of sufficient length and of sufficient materials to enable effective intramolecular probe hybridization. The length of the linker will typically be a length which is at least the length spanned by two nucleotide monomers, and preferably at least four nucleotide monomers, while not being so long as to interfere with either the pairing of the complementary (anti-parallel) intramolecularly hybridizing probe sequences. The flexible linker can be DNA, RNA or any of a variety of chemical structures.

The test nucleic acid strand can be prepared by any methods known in the art (See generally, Ausubel (Ed.) *Current Protocols in Molecular Biology,* 2.11. *Synthesis and Purification of Oligonucleotides,* John Wiley & Sons, Inc. (2000)). A hairpin probe can be prepared by synthesizing a single polynucleotide. Alternatively, one can separately synthesize each portion of the probe involved in intramolecular hybridization and then couple the portions together as a single hairpin probe by conjugation to each end of a separately prepared flexible linker. In this case, the flexible linker includes a linking group typically an alkylene group (of from about 6 to about 24 carbons in length), a polyethyleneglycol group (of from about 2 to about 24 ethyleneglycol monomers in a linear configuration), a polyalcohol group, a polyamine group (e.g., spermine, spermidine and polymeric derivatives thereof), a polyester group (e.g., poly(ethyl acrylate) having from about 3 to 15 ethyl acrylate monomers in a linear configuration), a polyphosphodiester group, or a polynucleotide (having from about 2 to about 12 nucleic acids). Preferably, the linking group will be a polyethyleneglycol group which is at least a tetraethyleneglycol, and more preferably, from about 1 to 4 hexaethyleneglycols linked in a linear array.

When synthesizing the hairpin probe from a separate flexible linker and separate intrahybridizing sequence portions of the hairpin probe, the flexible linker will be provided with functional groups at each end that can be suitably protected or activated. The functional groups are covalently attached to each portion of the probe via an ether, ester, carbamate, phosphate ester or amine linkage to either the 5'-hydroxyl or the 3'-hydroxyl of the probe portions chosen such that the complementary intramolecularly hybridizing sequences are in an anti-parallel configuration. Preferred linkages are phosphate ester linkages similar to typical oligonucleotide linkages. For example, hexaethyleneglycol can be protected on one terminus with a photolabile protecting group (i.e., NVOC or MeNPOC) and activated on the other terminus with 2-cyanoethyl-N,N-diisopropylaminochlorophosphite to form a phosphoramidite. This linking group can then be used for construction of the probe libraries in the same manner as photolabile-protected, phosphoramidite-activated nucleotides. Other methods of forming ether, carbamate or amine linkages are known to those of skill in the art and particular reagents and references can be found in such texts as March, Advanced Organic Chemistry, 4th Ed., Wiley-Interscience, New York, N.Y., 1992.

Alternatively, naturally occurring oligonucleotides, or fragments thereof, may be isolated from their natural sources or purchased from commercial sources. Probe oligonucleotides can be generally be from nucleotides in length, preferably from about 6 to about 50 nucleotides, although oligonucleotides of different length may be appropriate. Suitable oligonucleotides may be prepared by the phosphoramidite method described by Beaucage and Carruthers, *Tetrahedron Lett.*, 22:1859–1862 (1981), or by the triester method according to Matteucci et al., *J. Am. Chem. Soc.*, 103:3185 (1981), or by other chemical methods using either a commercial automated oligonucleotide synthesizer or by VLSIPS™ technology (discussed in detail below).

Hybridization Conditions

Any suitable conditions can be used for hybridizing the target DNA strand with the test nucleic acid strand comprising a sufficient number of ribonucleotide residues that span the position of said point mutation to be detected to form a target DNA strand/test nucleic acid strand duplex. For example, the target DNA strand and the test nucleic acid strand can be hybridized under the low, middle or high stringency.

If a hairpin probe is used as the test nucleic acid strand, any conditions that favor intermolecular hybridization between the probe and the target DNA sequence over intramolecular hybridization of the probe itself can be used in the present methods. Preferably, the conditions that favor intermolecular hybridization between the probe and the target DNA sequence over intramolecular hybridization of the probe itself is achieved by controlling compositions of the probe and the target DNA sequence so that the Tm of the intermolecular hybrid is higher than the Tm of the intramolecular hybrid. For example, the intermolecular hybrid can be a RNA:RNA hybrid, the intramolecular hybrid can be a RNA:DNA or a DNA:DNA hybrid. Alternatively, the intermolecular hybrid can be a RNA:DNA hybrid, the intramolecular hybrid can be a DNA:DNA hybrid. Normally, the Tm of the intermolecular hybrid is at least 2° C. higher than the Tm of the intramolecular hybrid. Preferably, the Tm of the intermolecular hybrid is at least 5° C. higher than the Tm of the intramolecular hybrid.

The hybridization between the hairpin probe and the target DNA sequence can be carried out at any suitable temperature. For example, the oligonucleotide probe and the target DNA sequence can be contacted at a temperature from about 4° C. to about 90° C. Preferably, the oligonucleotide probe and the target DNA sequence can be contacted at a temperature from about 25° C. to about 60° C. More preferably, the oligonucleotide probe and the target DNA sequence can be contacted at a temperature from about 35° C. to about 50° C.

The hybridization between the hairpin probe and the target DNA sequence can be carried out for any suitable period of time. For example, the oligonucleotide probe and the target DNA sequence can be contacted for a time from about 1 minute to about 60 minutes. Preferably, the oligonucleotide probe and the target DNA sequence can be contacted for a time from about 15 minutes to about 30 minutes.

The target DNA strand and/or test nucleic acid strand can exist in single or double stranded form. Preferably, prior to the hybridization action, the target DNA strand and/or test nucleic acid strand are processed to become single stranded. Although not preferred, the target DNA strand and the test nucleic acid strand can be hybridized in a single strand:double strand or a double strand:double strand hybridization reaction.

RNase H Cleavage

Any ribonuclease that has RNase H activity can be used in the present method. For example, a ribonuclease that has RNase H activity as its sole activity or one of its activities can be used. If a ribonuclease that has RNase H activity as one of its activities is used, other non-RNase H activities may preferably be inactivated.

In a specific embodiment, RNase H isolated from *E. coli* can be used (Berkower et al., *J. Biol. Chem.*, 248(17) :5914–21 (1973)). The RNase H or enzymes having RNase H activity that are disclosed in the following patents, published patent applications and literatures can also be used: U.S. Pat. Nos. 6,071,734 and 6,001,653; WO 99/28447, WO 98/07869; Crooke, *Antisense Nucleic Acid Drug Dev.*, 8(2) :133–4 (1998); Yang and Steitz, *Structure*, 3(2):13–14 (1995); and Papaphilis et al., *Anticancer Res.*, 10(5A) :1201–12 (1990). Commercially available RNase H or enzymes having RNase H activity can also be used.

The conditions for conducting RNase H cleavage is known in the art (See generally, Ausubel (Ed.) *Current Protocols in Molecular Biology*, 3.13.2. *Ribonuclease H*, John Wiley & Sons, Inc. (2000)). An exemplary reaction cocktail for conducting a RNase H cleavage reaction can contain the following components: a) 20 mM HERPES.KOH, pH 8.0; b) 50 mM KCl; c) 4 mM $MgCl_2$; d) 1 mM DTT; e) 2 μg/ml BSA; f) 1 unit RNase H. One unit of RNase H is normally defined as the amount of enzyme that produces 1 nmol of acid-soluble ribonucleotides from poly(A):poly(dT) in 20 minutes at 37° C. The incubation can be conducted at 37° C. for 20 minutes. The reaction can be stopped by adding 1 μl of 0.5 M EDTA. The volume of reaction, amount of nucleic acid, units of enzymes, temperature, time and method of stopping of reaction will vary depending on the application.

Detection of the RNase H Cleavage

The cleavage of the ribonucleotide residues by RNase H can be assessed by suitable methods. For example, the cleavage of the ribonucleotide residues can be assessed by analyzing the disappearance of the target DNA strand/test nucleic acid strand duplex, e.g., by gel electrophoresis. Alternatively, the cleavage of the ribonucleotide residues can be assessed by analyzing the cleavage product(s).

Any type of gel electrophoresis, including agarose gel electrophoresis, pulsed-field gel electrophoresis, capillary electrophoresis and polyacrylamide gel electrophoresis, can be used (See generally, Ausubel (Ed.) *Current Protocols in Molecular Biology*, 2. *Preparation and Analysis of DNA and* 4. *Preparation and Analysis of RNA*, John Wiley & Sons, Inc. (2000)). Other suitable analytical methods such as mass spectrometry, chromatograph, filtration and centrifugation can also be used. In a preferred embodiment, each of the target DNA strand and the test nucleic acid strand contains an element, whereby the formation of the target DNA strand/test nucleic acid strand duplex brings the two elements into close proximity to generate a detectable signal, and the cleavage of the ribonucleotide residues disrupts or interferes with the close proximity of the two elements and alters the detectable signal. More preferably, the elements belong to an enzyme/substrate pair or are components of a fluorescence resonance energy transfer (FRET) system.

Any FRET detection system known in the art can be used in the present TM method. For example, the AlphaScreen system can be used. AlphaScreen technology is an "Amplified Luminescent Proximity Homogeneous Assay" method. Upon illumination with laser light at 680 nm, a photosensitizer in the donor bead converts ambient oxygen to singlet-state oxygen. The excited singlet-state oxygen molecules diffuse approximately 250 nm (one bead diameter) before rapidly decaying. If the acceptor bead is in close proximity of the donor bead, by virtue of a biological interaction, the singlet-state oxygen molecules reacts with chemiluminescent groups in the acceptor beads, which immediately transfer energy to fluorescent acceptors in the same bead. These fluorescent acceptors shift the emission wavelength to 520–620 nm. The whole reaction has a 0.3 second half-life of decay, so measurement can take place in time-resolved mode. Other exemplary FRET donor/acceptor pairs include Fluorescein (donor) and tetramethylrhodamine (acceptor) with an effective distance of 55 Å; IAEDANS (donor) and Fluorescein (acceptor) with an effective distance of 46 Å; and Fluorescein (donor) and QSY-7 dye (acceptor) with an effective distance of 61 Å (Molecular Probes).

Test Samples and Target DNA Sequences

Any target DNA sequences, whether naturally occurring, synthetic or a combination thereof, can be assayed by the present method.

In a preferred embodiment, the target DNA strand is amplified before being contacted with the test nucleic acid strand. Any suitable DNA amplification methods can be used to amplify the target DNA strand. For example, the target DNA can be amplification products of any known nucleic acid amplification methods such as polymerase chain reaction (PCR) (U.S. Pat. Nos. 4,683,195 and 4,683,202 and Ausubel (Ed.) *Current Protocols in Molecular Biology*, 15. *The Polymerase Chain Reaction,* John Wiley & Sons, Inc. (2000)), ligase chain reaction (LCR), nucleic acid sequence-based amplification (NASBA) (U.S. Pat. Nos. 5,409,818 and 5,554,517), strand displacement amplification (SDA) and transcription-medicated amplification (TMA).

Target DNA sequences from any suitable sample can be assayed by the present method. Preferably, the target DNA strand is derived from a biosample. Test samples can include body fluids, such as urine, blood, semen, cerebrospinal fluid, pus, amniotic fluid, tears, or semisolid or fluid discharge, e.g., sputum, saliva, lung aspirate, vaginal or urethral discharge, stool or solid tissue samples, such as a biopsy or chorionic villi specimens. Test samples also include samples collected with swabs from the skin, genitalia, or throat. Test samples can be processed to isolate nucleic acid by a variety of means well known in the art (See generally, Ausubel (Ed.) *Current Protocols in Molecular Biology*, 2. *Preparation and Analysis of DNA and* 4. *Preparation and Analysis of RNA*, John Wiley & Sons, Inc. (2000)).

Although the present method can be used in solution, it is preferably conducted in chip format, e.g., by using the probe(s) immobilized on a solid support.

Similarly, although the present method can be used to analyze a single sample with a single probe at a time. Preferably, the method is conducted in high-throughput format. For example, a plurality of samples can be analyzed with a single probe simultaneously, or a single sample can be analyzed using a plurality of probes simultaneously. More preferably, a plurality of samples can be analyzed using a plurality of probes simultaneously.

Any suitable samples can be analyzed using the present method. Preferably, a biosample is analyzed using the present method. For example, a biosample of plant, animal, human, fungal, bacterial and viral origin can analyzed. If a sample of a mammalian or human origin is analyzed, the sample can be derived from a particular tissue or organ. Exemplary tissues include connective, epithelium, muscle or nerve tissue. Exemplary organs include eye, annulospiral organ, auditory organ, Chievitz organ, circumventricular organ, Corti organ, critical organ, enamel organ, end organ, external female gential organ, external male genital organ, floating organ, flower-spray organ of Ruffini, genital organ, Golgi tendon organ, gustatory organ, organ of hearing, internal female genital organ, internal male genital organ, intromittent organ, Jacobson organ, neurohemal organ, neurotendinous organ, olfactory organ, otolithic organ, ptotic organ, organ of Rosenmüller, sense organ, organ of smell, spiral organ, subcommissural organ, subfornical organ, supernumerary organ, tactile organ, target organ, organ of taste, organ of touch, urinary organ, vascular organ of lamina terminalis, vestibular organ, vestibulocochlear organ, vestigial organ, organ of vision, visual organ, vomeronasal organ, wandering organ, Weber organ and organ of Zuckerkandl. Preferably, samples derived from an internal mammalian organ such as brain, lung, liver, spleen, bone marrow, thymus, heart, lymph, blood, bone, cartilage, pancreas, kidney, gall bladder, stomach, intestine, testis, ovary, uterus, rectum, nervous system, gland, internal blood vessels, etc, are analyzed.

Alternatively, pathological samples in connection with various diseases or disorders or infections can be analyzed. Exemplary diseases or disorders include neoplasms (neoplasia), cancers, immune system diseases or disorders, metabolism diseases or disorder, muscle and bone diseases or disorders, nervous system diseases or disorders, signal diseases or disorders and transporter diseases or disorders. The infection to be analyzed can be fungal, bacterial and viral infection.

The present methods can be used to detect or analyze any nucleic acids from essentially any species of organism, including, for example, Acintobacter, Actinomyces, Aerococcus, Aeromonas, Alclaigenes, Bacillus, Bacteriodes, Bordetella, Branhamella, Bevibacterium, Campylobacter, Candida, Capnocytophagia, Chlamydia, Chromobacterium, Clostridium, Corynebacterium, Cryptococcus, Deinococcus, Enterococcus, Erysielothrix, Escherichia, Flavobacterium, Gemella, Gonorrhea, Haemophilus, Klebsiella, Lactobacillus, Lactococcus, Legionella, Leuconostoc, Listeria, Micrococcus, Mycobacterium, Neisseria, Nocardia, Oerskovia, Paracoccus, Pediococcus, Peptostreptococcus, Propionibacterium, Proteus, Psuedomonas, Rahnella, Rhodococcus, Rhodospirillium, Staphlococcus, Streptomyces, Streptococcus, Vibrio, and Yersinia. Also included are viruses such as the hepatitis viruses and human immunodeficiency viruses (HIV).

In a specific embodiment, the point mutation to be detected is a single nucleotide polymorphism. Preferably, a polymorphism in a genome, e.g., a viral, bacterial, eukaryotic, mammalian or human genome, is detected by the present methods. For example, human carbamyl phosphate synthetase I polymorphism (WO 00/73322), pen polymorphism of human platelet membrane glycoprotein IIIA (U.S. Pat. Nos. 5,972,601 and 5,670,337), human airway trypsin protease gene polymorphism (WO 99/31271), polymorphism of human cytochrome P4501A2 (U.S. Pat. No. 5,719,026), Bak polymorphism of human platelet membrane glycoprotein IIb (U.S. Pat. No. 5,652,357) and polymorphism of human cytochrome P4502D6 (WO 95/30772) can be detected by the present method. The human genome SNPs listed on the World Wide Web at "ncbi.nlm.nih.gov/SNP" can also be detected by the present method.

C. Kits and Arrays

In another aspect, the present invention provides a kit for detecting a point mutation in a DNA strand, which kit comprises: a) a test nucleic acid strand that is complementary to a target DNA strand containing or suspected of containing a point mutation to be detected and capable of forming a target DNA strand/test nucleic acid strand duplex, said test nucleic acid strand comprising a sufficient number of ribonucleotide residues to span the position of said point mutation to be detected; and b) an RNase H.

Any suitable test nucleic acid strand comprising a sufficient number of ribonucleotide residues that span the position of said point mutation to be detected and RNase H, including the ones disclosed in the above Section B, can be used in the present kit. Preferably, the sufficient number of ribonucleotide residues within the test nucleic acid strand comprises at least a ribonucleotide sequence having the formula 5'-RXR-3', 5'-RRX-3' or 5'-RRXR-3', or a complementary strand thereof, wherein R is an ribonucleotide residue complementary to its corresponding deoxyribonucleotide in said target DNA strand and X represents the position of said point mutation to be detected and X is an ribonucleotide residue that is complementary or not complementary to its corresponding deoxyribonucleotide in said target DNA strand.

In another preferred embodiment, the kit can further comprise an instruction for detecting a point mutation in a DNA strand using the test nucleic acid strand and the RNase H.

In still another aspect, the present invention provides an array of test nucleic acid strands immobilized on a solid support for detecting a point mutation in a DNA strand, comprising a solid support suitable for use in nucleic acid hybridization having immobilized thereon a plurality of test nucleic acid strands, at least one of the test nucleic acid strands comprising a sufficient number of ribonucleotide residues to span the position of said point mutation to be detected to form a target DNA strand/test nucleic acid strand duplex. Preferably, at least half or all of the test nucleic acid strands comprise a sufficient number of ribonucleotide residues that span the position of said point mutation to be detected to form a target DNA strand/test nucleic acid strand duplex.

Any suitable test nucleic acid strand comprising a sufficient number of ribonucleotide residues that span the position of said point mutation to be detected, including the ones disclosed in the above Section B, can be used in the present array. Preferably, the sufficient number of ribonucleotide residues within at least one of the test nucleic acid strands comprises at least a ribonucleotide sequence having the formula 5'-RXR-3', 5'-RRX-3' or 5'-RRXR-3', or a complementary strand thereof, wherein R is an ribonucleotide residue complementary to its corresponding deoxyribonucleotide in said target DNA strand and X represents the position of said point mutation to be detected and X is an ribonucleotide residue that is complementary or not complementary to its corresponding deoxyribonucleotide in said target DNA strand. More preferably, at least half or all of the test nucleic acid strands comprises at least a ribonucleotide sequence having the formula 5'-RXR-3', 5'-RRX-3' or 5'-RRXR-3', or a complementary strand thereof, wherein R is an ribonucleotide residue complementary to its corresponding deoxyribonucleotide in said target DNA strand and X represents the position of said point mutation to be detected and X is an ribonucleotide residue that is complementary or not complementary to its corresponding deoxyribonucleotide in said target DNA strand.

In another preferred embodiment, each of the test nucleic acid strands is capable of forming a target DNA strand/test nucleic acid strand duplex with a different target DNA strand.

Immobilization of Test Nucleic Acid Strands

The test nucleic acid strands used in the present array or kit can be immobilized on any solid support that is suitable for use in nucleic acid hybridization. The solid support may be biological, nonbiological, organic, inorganic, or a combination of any of these, existing as particles, strands, precipitates, gels, sheets, tubing, spheres, containers, capillaries, pads, slices, films, plates, slides, etc.

A solid support for immobilizing probes is preferably flat, but may take on alternative surface configurations. For example, the solid support may contain raised or depressed regions on which probe synthesis takes place or where probes are attached. In some embodiments, the solid support can be chosen to provide appropriate light-absorbing characteristics. For example, the support may be a polymerized Langmuir Blodgett film, glass or functionalized glass, Si, Ge, GaAs, GaP, $SiO_2$, $SiN_4$, modified silicon, or any one of a variety of gels or polymers such as (poly)tetrafluoroethylene, (poly)vinylidendifluoride, polystyrene, polycarbonate, or combinations thereof. Other suitable solid support materials will be readily apparent to those of skill in the art.

The surface of the solid support can contain reactive groups, which could be carboxyl, amino, hydroxyl, thiol, or the like suitable for conjugating to a reactive group associated with an oligonucleotide or a nucleic acid. Preferably, the surface is optically transparent and will have surface Si—OH functionalities, such as are found on silica surfaces.

The test nucleic acid strands, e.g., hairpin probes, can be attached to the solid support by chemical or physical means such as through ionic, covalent or other forces well known in the art. Immobilization of nucleic acids and oligonucleotides can be achieved by means well known in the art (see, e.g., Dattagupta et al., *Analytical Biochemistry*, 177:85–89 (1989); Saiki et al., *Proc. Natl. Acad. Sci. USA*, 86:6230–6234(1989); and Gravitt et al., *J. Clin. Micro.*, 36:3020–3027(1998)).

The test nucleic acid strands, e.g., hairpin probes, can be attached to a solid support by means of a spacer molecule, e.g., essentially as described in U.S. Pat. No. 5,556,752 to Lockhart et al., to provide space between the double stranded portion of the probe as may be helpful in hybridization assays. A spacer molecule typically comprises between 6–50 atoms in length and includes a surface attaching portion that attaches to the solid support. Attachment to the support can be accomplished by carbon—carbon bonds using, for example, supports having (poly) trifluorochloroethylene surfaces, or preferably, by siloxane bonds (using, for example, glass or silicon oxide as the solid support). Siloxane bonding can be formed by reacting the support with trichlorosilyl or trialkoxysilyl groups of the spacer. Aminoalkylsilanes and hydroxyalkylsilanes, bis(2-hydroxyethyl)-aminopropyltriethoxysilane, 2-hydroxyethylaminopropyltriethoxysilane, aminopropyltriethoxysilane or hydroxypropyltriethoxysilane are useful are surface attaching groups.

The spacer can also include an extended portion or longer chain portion that is attached to the surface attaching portion of the probe. For example, amines, hydroxyl, thiol, and carboxyl groups are suitable for attaching the extended portion of the spacer to the surface attaching portion. The extended portion of the spacer can be any of a variety of molecules which are inert to any subsequent conditions for polymer synthesis. These longer chain portions will typically be aryl acetylene, ethylene glycol oligomers containing 2–14 monomer units, diamines, diacids, amino acids, peptides, or combinations thereof.

In some embodiments, the extended portion of the spacer is a polynucleotide or the entire spacer can be a polynucleotide. The extended portion of the spacer also can be constructed of polyethyleneglycols, polynucleotides, alkylene, polyalcohol, polyester, polyamine, polyphosphodiester and combinations thereof. Additionally, for use in synthesis of probes, the spacer can have a protecting group, attached to a functional group, e.g., hydroxyl, amino or carboxylic acid) on the distal or terminal end of the spacer (opposite the solid support). After deprotection and coupling, the distal end can be covalently bound to an oligomer or probe.

Microarray Formation

A variety of the test nucleic acid strands, e.g., hairpin probes, can be attached to a single solid support to form a microarray by procedures well known in the art. This is also referred to as a "microarray biochip" or "nucleic acid biochip" or "DNA biochip."

A microarry biochip containing a library of probes can be prepared by a number of well known approaches including, for example, light-directed methods, such as VLSIPS™ described in U.S. Pat. Nos. 5,143,854, 5,384,261 or 5,561,071; bead based methods such as described in U.S. Pat. No. 5,541,061; and pin based methods such as detailed in U.S. Pat. No. 5,288,514. U.S. Pat. No. 5,556,752 to Lockhart, which details the preparation of a library of different double stranded probes as a microarray using the VLSIPS™ also is suitable for preparing a library of hairpin probes in a microarray.

Flow channel methods, such as described in U.S. Pat. Nos. 5,677,195 and 5,384,261, can be used to prepare a microarray biochip having a variety of different hairpin probes. In this case, certain activated regions of the substrate are mechanically separated from other regions when the probes are delivered through a flow channel to the support. A detailed description of the flow channel method can be found in U.S. Pat. No. 5,556,752 to Lockhart et al., including the use of protective coating wetting facilitators to enhance the directed channeling of liquids though designated flow paths.

Spotting methods also can be used to prepare a microarry biochip with a variety of hairpin probes immobilized thereon. In this case, reactants are delivered by directly depositing relatively small quantities in selected regions of the support. In some steps, of course, the entire support surface can be sprayed or otherwise coated with a particular solution. In particular formats, a dispenser moves from region to region, depositing only as much probe or other reagent as necessary at each stop. Typical dispensers include a micropipette, nanopippette, ink-jet type cartridge or pin to deliver the probe containing solution or other fluid to the support and, optionally, a robotic system to control the position of these delivery devices with respect to the support. In other formats, the dispenser includes a series of tubes or multiple well trays, a manifold, and an array of delivery devices so that various reagents can be delivered to the reaction regions simultaneously. Spotting methods are well known in the art and include, for example those described in U.S. Pat. Nos. 5,288,514, 5,312,233 and 6,024,138. In some cases, a combination of flowing channel and "spotting" on predefined regions of the support also can be used to prepare microarry biochips with immobilized hairpin probes.

D. EXAMPLES

Example 1

Human Papilloma Virus Genotyping

Immobilization of nucleic acids and oligonucleotides are known in the art (Dattagupta et al., *Analytical Biochemistry*, 177:85–89 (1989); Saiki et al., *Proc. Natl. Acad Sci., USA*, 86:6230–6234 (1989); and Gravitt et al., *J. Clin. Micro.*, 36:3020–3027 (1998)). Methods described in those references can be used in the present invention. human papilloma virus (HPV) probe sequences as described in Gravitt et al., (supra) are synthesized in a commercially available oligonucleotide synthesizer. During the synthesis, following changes are made:

i) The probes are extended at the 3' end up to 30 extra nucleotide residues. First 9 residues are made of dT to function as spacer for the hairpin structure.

ii) The rest (21 residues) is complementary to the probe sequence and sequentially organized as 7 deoxy-6 ribo-8 deoxy residues.

iii) The probe sequence has methylphosphonates complementary to the ribose residues in the chain. This will prevent RNase H digestion of the unhybridized hairpin probe. This will also reduce the Tm of the probe compared to an RNA-DNA hybrid formed with a target.

For example, the probe 5'-CAT CCG TAA CTA CAT CTT CCA-3' (SEQ ID NO:1) is present in an oligonucleotide of the following structure: 5'-CAT-CCG-TAa-cta-caT-CTT-CCA-TTT-TTT-TTT-TGG-AAG A TG-TAG-T TA-CGG-ATG-3' (SEQ ID NO:2) (underlined nucleotides are ribonucleotides, lower case nucleotides are methylphosphonates residues). Such an oligonucleotide is immobilized onto a membrane by BSA conjugation method and genomic HPV DNA is purified from samples by proteinase K digestion and ethanol precipitation as described in Gravitt et al (supra). The immobilized hairpin probe containing strip is hybridized with the sample DNA at 53° C. overnight in a buffer containing 0.72 M NaCl, 40 mM NaH$_2$PO$_4$ and 4 mM EDTA (pH 7.7). After hybridization, the strip is washed twice with the hybridization buffer at 57° C. and RNase H buffer once. The strip containing the hybrid is then treated with RNase H to digest the part of the hybridized probe with RNA-DNA hybrid structure. This is carried out by using 1 unit of RNase H from Sigma Chemical Co. (St. Louis, Mo.) per ml of the digestion buffer. The RNase H digestion buffer contains 20 mM tris-HCl (pH 7.5), 100 mM KCl, 10 mM $MgCl_2$, 0.1 mM EDTA, 0.1 mM DTT and 0.05 mg BSA per ml. By immersing the strip containing the hybrid in the digestion buffer containing the enzyme for 1 hour at 37° C., hybrids containing RNA-DNA structure is digested and under these conditions hairpin intra-molecular hybrid is not disturbed.

After the enzyme digestion, the strip is washed with hybridization buffer and a second hybridization is carried out with biotin labeled probes. The labeled probes are equal weight by weight mixtures of oligonucleotides complementary to the immobilized probe portions which become single stranded after hybridization and digestion. After the second hybridization and washing, biotin in the hybrid is detected by using a streptavidin-horseradish peroxidase conjugate chemiluminescence. This is carried out by soaking the array in a solution containing 1:1 mixture of 0.5 mM Luminol and hydrogen peroxide and wrapping the whole contents with a plastic wrap, e.g., "SARAN WRAP". The light emission is recorded on a "POLAROID" film. Biotin sites appear as white spots on the film.

The sites where biotin is detected is the site of hybridization of the target sample and the corresponding sequence is the sequence of the target present in the sample.

Example 2

Assay for Mycobacterium TB Drug Resistance by Post Hybridization Blocking of Immobilized Probes Using the sequence information disclosed in Telenti et al., Lancet, 341:647–650 (1993), Beenhouwer et al., Tubercule and Lung Disease, 76:425–430 (1995) designed PCR primers and probes for detection of mutated sequence in a rifampicin resistance of mycobacterium tuberculosis organism. The present method uses identical primers for PCR and immobilized probe sequences. The probe sequences are extended as described in example 1 to have a hairpin structure which is immobilized and at nucleotide position 45 a psoralen moiety is covalently attached.

Primer sequences for amplification are:
5'GAG AAT TCG GTC GGC GAG CTG ATCC 3' (SEQ ID NO:3)
and
5' CGA AGC TTG ACC CGC GCG TAC ACC 3' (SEQ ID NO:4).

These primers produce a 395 bp amplicon after PCR. PCR is done in a buffer containing 50 mM KCl, 10 mM tris-HCl (pH 8.3), 2.2 mM $MgCl_2$, 200 mM each of four dNTPs, 0.01% gelatin and 1U of Taq Polymerase. Typical amplification is done for 40 cycles (94° C., 58° C. and 72° C. at 45 sec.) For the synthesis of labeled amplicons as detection probe, PCR is done by using a mixture of dNTPs containing biotinylated dUTP and TTP in a 1:10 mixture and others in the same concentrations as above.

A typical 48-mer long hairpin probe has the following structure after immobilization:
5'**CAA TTC ATG GAC CAG AAC AAC CCG TTT TTT TTT CGG GTT GTT CTG CTC CAT GAA TTG 3' (SEQ ID NO:5). The sequence underlined is synthesized in an oligonucleotide synthesizer. In between nucleotides TT a psoralen modification is used to crosslink unhybridized hairpin probe after hybridization with the sample. First, the oligonucleotide with an amino terminated linker in the TT position is synthesized in a synthesizer. Such linkers have been described in U.S. Pat. No. 5,541,313. The amino terminated linker containing oligonucleotide is then reacted with an N-hydroxysuccinimide (NHS) activated 4'-carboxtrioxsalen derivative in dimethyl sulfoxide. Such a compound is synthesized by reacting 4'-aminomethyl trioxsalen (Sigma Chemical Co. St. Louis, Mo.) with succinic anhybride. The resulting carboxy compound is then further activated to produce NHS-ester which is used for the reaction. After the reaction the oligonucleotide is purified on a reverse phase HPLC column. The oligonucleotide is then phosphorylated at the 5'-end by conventional method using polynucleotide kinase. The solid support containing immobilized oligonucleotide of structure 5'-TTT TTT TTT CAA TTC ATG-3' (SEQ ID NO:6) is hybridized with 5'-phosphorylated GAC CAG AAC AAC CCG TTT TTT TTT CGG GTT GTT CTG CTC CAT GAA TTG-3' (SEQ ID NO:7). The hybrid is ligated by using a T4 DNA ligase. This produces an immobilized probe with a photo-crosslinking moiety.

A set of immobilized probes on polystyrene beads with sequences of all different modifications representative of the mutations responsible for rifampicin resistance is prepared as describe above. Each immobilized probe is dispensed in a microtitre plate well. Five microliters of the amplicons are aliquoted into each well followed by 40 microliters of hybridization buffer of example 1. Hybridization is done at 56° C. for 60 minutes. After hybridization the beads are washed as described in example 1. The microtiter plate is exposed to 312 nm light for 60 minutes using a transilluminator at 25° C. This process crosslinks all unhybridized immobilized probes and hybrid(s) to the solid support. The hybrids are detected by a second hybridization with a labeled probe as the PCR amplicon containing biotin as described above. Biotin in the hybrid is detected by a streptavidin-horseradish peroxidase enzyme system.

Example 3

Post Hybridization Labeling of Hybrids

Example 2 is repeated without the use of biotinylated labeled amplicon. After hybridization, washing and irradiation, the hybrids are labeled for detection by hybridization with an aminomethyl trioxsalen and enzyme labeled degenerate pentamer oligonucleotides. The double labeled oligonucleotides are synthesized as follows:

First, a psoralen labeled ribonucleotide is synthesized as described in Dattagupta et al., U.S. Pat. No. 5,587,472. Commercially available aminomethyltrioxsalen from Sigma Chemical Co. is derivatized with a dibasic acid anhydride like succinic anhydride. The resulting acid is mixed with (1:3:3 molar ratio) 1-(3-dimethylaminopropyl)-3-ethylcarbodimide methiodide and N-hydroxysulfosuccinimide (sodium salt) in DMF and heated to 50° C. for 7.5 hours. According to TLC (toluene/ethanol 0.5:4, silicagel), most of the carboxylic acid has been converted to the N-hydroxysulfosuccininimide ester. The reaction mixture is cooled to room temperature and a solution of 8-(6-aminohexyl) mninoadenosine-5'-triphosphate (Li-salt, Sigma, $10^{-5}$ mol) in 100 μl water and 20 μl pyridine ($2.5 \times 10^{-4}$ mol) is added. After stirring at room temperature overnight, only traces of a new compound are detectable. The mixture is then sonicated for 3 hours, 2 mg of 4-dimethylaminopyridine ($1.6 \times 10^{-5}$) is added and the mixture is sonicated for an additional 5 hours. According to TLC (t-BuOH 3.5/acetone 2.5/conc. ammonia 1.5/HOAc 1.5/water, cellulose), a new product is now easily detectable. The reaction mixture is evaporated to dryness under vacuum. Chromatography of the residue (3 times) on a Sephadex G10 column (Pharmacia) with water as eluent gives aminomethyltrioxsalen labeled ATP (ps-ATP).

The psoralen labeled ribonucleotide (ps-ATP described above) is incorporated into degenerate tetramer oligonucleotides by terminal deoxynucleotidyl transferase (Pharmacia) as follows:

1.8 µg oligonucleotide (synthesized in an Applied Biosystems Inc.'s (Foster City, Calif.) automated oligonucleotide synthesizer using their reagents) and 2.5 µg ps-ATP are dissolved in a reaction buffer containing 140 mmol/K-cacodylate, 30 mmol/l Tris-buffer (pH 7.6), 1 mmol/l cobalt chloride and 0.1 mmol/l dithiothreitol (DTT) (total volume 50 µl). Enzymatic elongation is achieved by addition of 22 U terminal deoxynucleotidyl transferase and incubation for 16.5 hours at 37° C.

20% denaturing polyacrylamide gel electrophoresis shows a DNA band under UV shadowing which can be detected visually.

ps-ATP labeled oligonucleotide is further treated if necessary, with sodium hydroxide to digest all but the last ribonucleotide residue which contains one aminomethyl trioxsalen moiety.

Similar method can be used to synthesize oligonucleotide with any ribonucleotide (A,U,G, C riboT or any other ribonucleoside or deoxyribonucleoside) at its 3' end.

All different degenerate sequences are made in a synthesizer. At the 3'-end of the pentamer, a psoralen moiety as described above and at the 5'-end an enzyme like horseradish peroxidase is covalently attached following the method described in U.S. Pat. No. 5,541,313. Such synthetic molecules are available commercially from Gemini Biotech Ltd. The Woodlands, Tex. These degenerate sequences hybridize to any complementary hybridizable sequence at 30° C. After hybridization and a second irradiation, the labeled petamers are covalently linked to the hybrid or single stranded hybridized probes. Unreacted pentamers are washed at 37° C. and hybrids are detected by the enzyme assay as described above.

Example 4

The Minimum Number of Ribonucleotides in DNA/RNA Chimeric Oligonucleotide for RNase H Cleavage RNase H hydrolyzes RNA strand in an RNA-DNA duplex. RNase H can also hydrolyze a short ribonucleotide stretch in a DNA-RNA-DNA fragment, when such DNA-RNA-DNA fragment binds with a complementary DNA strand. In order to determine the minimum number of ribonucleotides to be cleaved by RNase H in the DNA-RNA-DNA fragment, four kinds of oligonucleotides with different number of ribonucleotides (bold and underlined) were designed, AGT02008: 5'-TTTTTTT AAAATTTTTTTT-3' (SEQ ID NO:8), AGT02012: 5'-TTTTTTTAAAATTTTTTTT-3' (SEQ ID NO:9), AGT02013: 5'-TTTTTTTAAAATTTTTTTT-3' (SEQ ID NO:10) and AGT02014: 5'-TTTTTTTAAAA-TTTTTTTT-3' (SEQ ID NO:11). These oligos were mixed with a complement DNA oligo AGT02009: 5'-AAAAAAAATTTTAAAAAAA-3' (SEQ ID NO:12) at 37° C. for 25 minutes. Five units of RNase H were added and incubated at 37° C. for 30 minutes. FIG. 3A shows that RNase H can cleave four (4) ribonucleotides in the DNA/RNA chimeric oligo (comparing lane 2 with lanes 4, 6, and 8 of FIG. 3A.). With high concentration, e.g., about 50 units/µl, three (3) ribonucleotides can also be cut by RNase H (see lane 6 of FIG. 3B.). Two (2) ribonucleotides in the DNA/RNA chimeric oligo cannot be cut by RNase H under any condition. Therefore, four (4) ribonucleotides are the minimum numbers for RNase H cleavage with normal RNase H concentration, e.g., about 5 units/µl.

Example 5

Mismatch Inhibits RNase H Activity

A hairpin DNA probe contains a loop region and a stem region. When the target DNA (complement DNA) binds with the hairpin DNA probe, they can open the hairpin structure in the hairpin probe to form a duplex structure. If the target DNA doesn't complement to at least a portion of the sequence of the hairpin DNA probe, the hairpin DNA probe maintains its hairpin structure. If a RNase H cleavage site is present in the stem region, some modifications in hairpin DNA probe are need to inhibit the RNase H cleavage. When the hairpin probe binds with the target DNA, the duplex formed between the hairpin probe containing the RNase H cleavage site and the target DNA strand can be cleaved by RNase H. If the target DNA does not bind to the hairpin probe, the hairpin probe maintains original hairpin structure and cannot be cleaved by RNase H. Accordingly, the binding and non-binding between the hairpin probe and the target DNA strand can be determined by assessing RNase H cleavage. In order to find a condition that ablates RNase H cleavage, oligos AGT02020: 5'-AAAAAAAAATTTGAAAAAAA-3' (SEQ ID NO:13), AGT02021: 5'-AAAAAAAAATTGTAAAAAAA-3' (SEQ ID NO:14), AGT02022: 5'AAAAAAAAATTGG-AAAAAAA-3' (SEQ ID NO:15) and AGT02023: 5'AAAAAAAAATGTGAAAAAAA-3' (SEQ ID NO:16) containing mismatch(es) to the target DNA sequence were tested in the hybridization/RNase H cleavage assay. The oligos were mixed with the target DNA oligo AGT02009 (SEQ ID NO:12) at 37° C. for 25 minutes. One (1) unit of RNase H was added and incubated at 37° C. for 30 minutes. FIG. 4A. shows that two mismatch sites in the duplex ablated RNase H cleavage (Lanes 12 and 15 of FIG. 4A.). The effect of one mismatch site is less than two mismatch sites and it has polarity effect. The mutation site at position 2 has stronger inhibition effect than mutation site at position 3 (Comparing lanes 6 and 9 of FIG. 4A.). It was also found that there is no sequence preference at position 2 to inhibit RNase H cleavage because the tests using oligos AGT02021 (SEQ ID NO:14), AGT02024: 5'-AAAAAAAAA-TTCTAAAAAAA-3' (SEQ ID NO:17) and AGT02025: 5'-AAAAAAAAATTATAAAAAAA-3' (SEQ ID NO: 18) containing different mismatches at the same position gave similar blocking effect (See FIG. 4B).

Example 6

RNase H Can Be Used in Hairpin Structure Cleavage Assay

Linear probes were used in the experiments described in Examples 4 and 5. In this experiment, two hairpin DNA probes containing 4 ribonucleotides in 5' and 3' double stranded region (relative to the position of the single stranded loop region), AGT2010: GCACATTCTCAU-CUCTGAAAACTTCCGTGGTTTCAGAGAT-GAGAATGTGC (SEQ ID NO: 19) (the loop region is italicized) and AGT02011: GCACATTCTCATCTCT-GAAAACTTCCGTGGTTTCAGAGAUGAGAATGTGC (SEQ ID NO:20) (the loop region is italicized) were used.

The hairpin probes, alone or mixed with their complement target DNA AGT2028: 5'-CCACGGAAGTTTTCA-GAATTGAGAATGTGC-3' (SEQ ID NO:21) and AGT02029: 5'-GCACATTCTCAGATCTGAAACCAC-GGAA-3' (SEQ ID NO:22), respectively, were heated to 94° C. for 2 minutes. The temperature was then lowered to different annealing temperatures for 15 minutes. One (1) unit of RNase H was added and incubated at 37° C. for 30 minutes. Lane 2 of FIGS. 5A. and 5B. show that both hairpin DNA probes were cleaved by RNase H and there is no difference whether the RNase H cleavage site is located in 5' or 3' end of the single stranded loop region. In contrast, the two mismatch sites within the target DNA ablated the RNase H cleavage (Lanes 3 to 7 of FIGS. 5A and 5B.). Surprisingly, different annealing temperatures do not affect duplex formation and/or RNase H cleavage inhibition.

Example 7

The Hairpin Probe Can Bind with Single Strand Target Oligo at a Wide Range of Temperatures The hairpin DNA probe AGT02011 (SEQ ID NO:20) was heated to 94° C. for 2 minutes, and annealed at 60° C. for 10 minutes to form the hairpin structure. AGT02011 was also mixed with the target single strand DNA AGT02028 (SEQ ID NO:21) at different annealing temperatures for 25 minutes. FIGS. 6A. and 6B. show that there is no difference in duplex formation between the hairpin probe and the target DNA at a wide range of annealing temperatures from 18° C. to 85° C. It indicates that the hairpin structure and duplex formation is essentially independent of annealing temperatures. Additional experiments were conducted to assess this effect of annealing time. Hairpin probe was mixed with the target DNA at room temperature for 1 to 5 minutes and then loaded into the gel. The result shows that the duplex was formed with annealing time as short as 1 minute (FIG. 6C, lane 3). Even when annealing was conducted at 4° C., the hairpin probe still bound with the target DNA to form a duplex (FIG. 6C lane 8).

Example 8

The Sequence Specificity of Hairpin Probe

Specificity is a very important factor for hybridization assay. The hairpin probe used in this experiment is AGT02011 (SEQ ID NO:20). Different target DNAs containing mismatches with AGT02011 in its loop region, stem region and the junction between the loop and the stem regions were tested on their effect on binding. AGT02029 (SEQ ID NO:22) has two mismatch sites in the stem region of AGT02011. AGT02039: 5' CATCAACTATC-AAGTGCAAACCACGGAAGT-3' (SEQ ID NO:23) is 100% match at loop region and 25% match in stem region of AGT02011. AGT02040: 5'-GCACATTCTCTCATC-TGAAGCTCCGTACT-3' (SEQ ID NO:24) is 50% match in loop region and 100% match in stem region of AGT02011. AGT02048: 5'-GCACATTCTCAGATCTGAAAGATCGGAAGT-3' (SEQ ID NO:25) has 3 mismatch sites in the junction of loop and stem regions of AGT02011. FIG. 7. shows that only AGT02029 can bind with AGT02011 to form the duplex form. The effect of mutation in the loop region seem to be more serious than mutation in the stem region (Comparing lanes 3 and 7 of FIG. 7.).

Example 9

The Loop Region of a Hairpin Probe Play an Important Role in Target Sequence Binding Three target DNAs with different length complementary to the loop region of the hairpin probe AGT02011 (SEQ ID NO:20) were used in this experiment. AGT02029 (SEQ ID NO:22), AGT02035: 5'-GCACATTCTCAGATCT-GAAACCACGGAAGT-3' (SEQ ID NO:26) and AGT02036: 5'-GCACATTCTCAGATCTGAAACC-3' (SEQ ID NO:27) have 8, 10 and 2 oligonucleotides that are complementary to the loop region of the hairpin probe AGT02011, respectively. FIG. 8. shows that AGT02036 can't bind to AGT02011 to form a duplex (See FIG. 8, lane 7). This result indicates that binding between the loop region of the hairpin probe with target DNA may help the hairpin to open at low temperature, e.g., about 4° C. Complementary of two nucleotides in the loop region to target DNA can't give enough energy to open the hairpin structure at low temperature.

The above examples are included for illustrative purposes only and is not intended to limit the scope of the invention. Since modifications will be apparent to those of skill in this art, it is intended that this invention be limited only by the scope of the appended claims.

What is claimed is:

1. A method for detecting a point mutation in a DNA strand, which method comprises:

a) hybridizing a target DNA strand containing or suspected of containing a point mutation with a test nucleic acid strand complementary to said DNA strand to form a target DNA strand/test nucleic acid strand duplex, said nucleic acid strand comprising a sufficient number of ribonucleotide residues to span the position of said point mutation to be detected;

b) contacting said target DNA strand/test nucleic acid strand duplex formed in step a) with an RNase H; and c) determining whether said ribonucleotide residues within said test nucleic acid strand are cleaved by said RNase H, wherein said ribonucleotide residues within said test nucleic acid strand are cleaved by said RNase H in the absence of mismatch at said position of said point mutation and said ribonucleotide residues within said test nucleic acid strand are not cleaved by said RNase H in the presence of mismatch at said position of said point mutation and the presence or absence of a point mutation in said target DNA is assessed; and wherein the test nucleic acid strand is a part of a hairpin probe having a loop and a stem regions, wherein the loop region has at least 3 nucleotide residues and the target DNA strand and the test nucleic acid strand are hybridized under conditions that favor intermolecular hybridization between the target DNA strand and the test nucleic acid strand over intramolecular hybridization of the test nucleic acid strand itself.

2. The method of claim 1, wherein the sufficient number of ribonucleotide residues that span the position of said point mutation to be detected is located within the loop or stem region of the hairpin probe.

3. The method of claim 1, the hairpin probe further comprises an element or a modification that facilitates intramolecular crosslinking of the test nucleic acid strand upon suitable treatment.

4. The method of claim 3, wherein the element is a chemically or photoactively activatable crosslinking agent.

5. The method of claim 4, wherein the photoactively activatable crosslinking agent is a furocoumarin.

6. The method of claim 4, wherein the element is a macromolecule having multiple ligand binding sites.

7. The method of claim 6, wherein the macromolecule is a component of biotin-avidin binding system.

8. The method of claim 1, wherein the conditions that favor intermolecular hybridization between the target DNA strand and the test nucleic acid strand over intramolecular hybridization of the test nucleic acid strand itself is achieved by controlling compositions of the target DNA strand and the test nucleic acid strand so that the Tm of the intermolecular hybrid is higher than the Tm of the intramolecular hybrid.

9. The method of claim 8, wherein the Tm of the intermolecular hybrid is at least 2° C. higher than the Tm of the intramolecular hybrid.

10. The method of claim 1, wherein the sufficient number of ribonucleotide residues within the test nucleic acid strand comprises at least a ribonucleotide sequence having the formula 5'-RXR-3', 5'-RRX-3' or 5'-RRXR-3', or a complementary strand thereof, wherein R is an ribonucleotide residue complementary to its corresponding deoxyribonucleotide in said target DNA strand and X represents the position of said point mutation to be detected and X is an ribonucleotide residue that is complementary or not complementary to its corresponding deoxyribonucleotide in said target DNA strand.

11. The method of claim 10, wherein X is complementary to the corresponding deoxyribonucleotide that would be present in a wild-type target DNA strand and cleavage of the ribonucleotide residues within the test nucleic acid strand indicates the absence of a point mutation at position X and failure of the cleavage of the ribonucleotide residues within the test nucleic acid strand indicates the presence of a point mutation at position X.

12. The method of claim 10, wherein X is not complementary to the corresponding deoxyribonucleotide that would be present in a wild-type target DNA strand and the cleavage of the ribonucleotide residues within the test nucleic acid strand indicates the presence of a point mutation at position X.

13. The method of claim 1, wherein the cleavage of the ribonucleotide residues is assessed by analyzing the disappearance of the target DNA strand/test nucleic acid strand duplex.

14. The method of claim 13, wherein the disappearance of the target DNA strand/test nucleic acid strand duplex is analyzed by gel electrophoresis.

15. The method of claim 1, wherein each of the target DNA strand and the test nucleic acid strand contains an element, whereby the formation of the target DNA strand/test nucleic acid strand duplex brings the two elements into close proximity to generate a detectable signal, and the cleavage of the ribonucleotide residues disrupts or interferes with the close proximity of the two elements and alters the detectable signal.

16. The method of claim 15, wherein the elements belong to an enzyme/substrate pair or are components of a fluorescence resonance energy transfer (FRET) system.

17. The method of claim 1, wherein the test nucleic acid strand is immobilized on a solid support.

18. The method of claim 1, wherein a plurality of the test nucleic acid strands immobilized on a solid support is used.

19. The method of claim 18, wherein each of the plurality of the test nucleic acid strands is capable of detecting a different point mutation.

20. The method of claim 18, wherein a plurality of samples is assayed simultaneously.

21. The method of claim 1, wherein the test nucleic acid strand comprises non-natural elements.

22. The method of claim 21, wherein the non-natural elements are non-natural bases, non-natural sugars, and/or non-natural phosphodiester linkages.

* * * * *